(12) United States Patent
MacEwan et al.

(10) Patent No.: US 12,201,749 B2
(45) Date of Patent: Jan. 21, 2025

(54) COMBINED MACRO AND MICRO-POROUS HYBRID-SCALE FIBER MATRIX

(71) Applicant: Acera Surgical, Inc., St. Louis, MO (US)

(72) Inventors: Matthew R. MacEwan, St. Louis, MO (US); Lily Jeng, St. Louis, MO (US); Abdolrasol Rahimi, St. Louis, MO (US); Manisha Jassal, St. Louis, MO (US); Tamas Kovacs, St. Louis, MO (US)

(73) Assignee: Acera Surgical, Inc., St. Louis, MO (US)

( * ) Notice: Subject to any disclaimer, the term of this patent is extended or adjusted under 35 U.S.C. 154(b) by 0 days.

(21) Appl. No.: 17/877,136

(22) Filed: Jul. 29, 2022

(65) Prior Publication Data

US 2023/0030107 A1 Feb. 2, 2023

Related U.S. Application Data

(60) Provisional application No. 63/203,731, filed on Jul. 29, 2021.

(51) Int. Cl.
| | |
|---|---|
| *A61L 27/60* | (2006.01) |
| *A61L 27/56* | (2006.01) |
| *D01D 5/00* | (2006.01) |
| *D04H 1/728* | (2012.01) |

(52) U.S. Cl.
CPC .............. *A61L 27/60* (2013.01); *A61L 27/56* (2013.01); *D01D 5/0076* (2013.01); *D04H 1/728* (2013.01)

(58) Field of Classification Search
CPC ....... A61L 27/60; A61L 27/56; D01D 5/0076; D04H 1/728; A61F 2/0063; A61F 2002/0068

See application file for complete search history.

(56) References Cited

U.S. PATENT DOCUMENTS

| | | | |
|---|---|---|---|
| 2,068,703 | A | 1/1937 | Powdermaker |
| 2,241,394 | A | 5/1941 | Duffy |
| 3,280,229 | A | 10/1966 | Simons |
| 3,338,992 | A | 8/1967 | Kinney |

(Continued)

FOREIGN PATENT DOCUMENTS

| | | |
|---|---|---|
| AU | 2011268321 A1 | 1/2013 |
| AU | 2012390291 A1 | 4/2015 |

(Continued)

OTHER PUBLICATIONS

Gibson, et al., "Electrospun Fiber Mats: Transport Properties." AIChE journal. 45. 190-195. Jan. 1999.

(Continued)

*Primary Examiner* — Brian A Dukert
*Assistant Examiner* — Rebecca Lynee Zimmerman
(74) *Attorney, Agent, or Firm* — VIA LLP

(57) ABSTRACT

Disclosed herein are embodiments of a non-woven hybrid-scale fiber matrix sheet which can be used to improve wound healing. The non-woven hybrid-scale fiber matrix sheet may be both microporous, due to the hybrid-scale fiber matrix, as well as macroporous through the addition of cuts or perforations in the hybrid-scale fiber matrix sheet. The micro and macroporous sheet can improve biological healing at a wound site.

19 Claims, 16 Drawing Sheets

(56) References Cited

U.S. PATENT DOCUMENTS

| | | |
|---|---|---|
| 3,341,394 A | 9/1967 | Kinney |
| 3,502,763 A | 3/1970 | Levy |
| 3,542,615 A | 11/1970 | Dobo et al. |
| 3,692,618 A | 9/1972 | Dorschner et al. |
| 3,740,302 A | 6/1973 | Soehngen |
| 3,802,817 A | 4/1974 | Matsuki et al. |
| 3,849,241 A | 11/1974 | Butin et al. |
| 3,909,009 A | 9/1975 | Cvetko et al. |
| 4,044,404 A | 8/1977 | Martin et al. |
| 4,340,563 A | 7/1982 | Appel et al. |
| 4,468,428 A | 8/1984 | Early et al. |
| 4,738,740 A | 4/1988 | Pinchuk et al. |
| 4,925,924 A | 5/1990 | Silver et al. |
| 4,965,110 A | 10/1990 | Berry |
| 5,024,789 A | 6/1991 | Berry |
| 5,036,551 A | 8/1991 | Dailey et al. |
| 5,079,080 A | 1/1992 | Schwarz |
| 5,306,550 A | 4/1994 | Nishiyama et al. |
| 5,464,450 A | 11/1995 | Buscemi et al. |
| 5,591,335 A | 1/1997 | Barboza et al. |
| 5,626,611 A | 5/1997 | Liu et al. |
| 5,634,944 A | 6/1997 | Magram |
| 5,735,863 A | 4/1998 | Della et al. |
| 5,795,584 A | 8/1998 | Totakura et al. |
| 5,851,937 A | 12/1998 | Wu et al. |
| 5,997,568 A | 12/1999 | Liu |
| 6,031,148 A | 2/2000 | Hayes et al. |
| 6,048,808 A | 4/2000 | Kurihara et al. |
| 6,147,135 A | 11/2000 | Yuan et al. |
| 6,162,535 A | 12/2000 | Turkevich et al. |
| 6,171,338 B1 | 1/2001 | Talja et al. |
| 6,180,848 B1 | 1/2001 | Flament et al. |
| 6,183,670 B1 | 2/2001 | Torobin et al. |
| 6,265,333 B1 | 7/2001 | Dzenis et al. |
| 6,306,424 B1 | 10/2001 | Vyakarnam et al. |
| 6,391,060 B1 | 5/2002 | Ory et al. |
| 6,596,296 B1 | 7/2003 | Nelson et al. |
| 6,630,231 B2 | 10/2003 | Perez et al. |
| 6,649,807 B2 | 11/2003 | Mizutani |
| 6,685,956 B2 | 2/2004 | Chu et al. |
| 6,689,374 B2 | 2/2004 | Chu et al. |
| 6,713,011 B2 | 3/2004 | Chu et al. |
| 6,753,454 B1 | 6/2004 | Smith et al. |
| 6,790,455 B2 | 9/2004 | Chu et al. |
| 6,797,655 B2 | 9/2004 | Rudisill et al. |
| 6,946,506 B2 | 9/2005 | Bond et al. |
| 7,134,857 B2 | 11/2006 | Andrady et al. |
| 7,172,765 B2 | 2/2007 | Chu et al. |
| 7,192,604 B2 | 3/2007 | Brown et al. |
| 7,655,070 B1 | 2/2010 | Dallas et al. |
| 7,759,082 B2 | 7/2010 | Bowlin et al. |
| 7,799,262 B1 | 9/2010 | Kim |
| 7,846,466 B2 | 12/2010 | Shea et al. |
| 7,879,093 B2 | 2/2011 | Wei et al. |
| 7,981,353 B2 | 7/2011 | Mitchell et al. |
| 8,066,932 B2 | 11/2011 | Xu |
| 8,222,166 B2 | 7/2012 | Chu et al. |
| 8,273,369 B2 | 9/2012 | Moloye-Olabisi et al. |
| 8,652,215 B2 | 2/2014 | Bellamkonda et al. |
| 8,728,463 B2 | 5/2014 | Atala et al. |
| 8,728,817 B2 | 5/2014 | Ogle et al. |
| 8,809,212 B1 | 8/2014 | Dirk et al. |
| 8,852,621 B2 | 10/2014 | Patel et al. |
| 9,074,172 B2 | 7/2015 | Johnson |
| 9,085,830 B2 | 7/2015 | Mitchell et al. |
| 9,163,331 B2 | 10/2015 | Atala et al. |
| 9,168,231 B2 | 10/2015 | Patel et al. |
| 9,345,486 B2 | 5/2016 | Zhang et al. |
| 9,393,097 B2 | 7/2016 | McCullen et al. |
| 9,476,026 B2 | 10/2016 | Arinzeh et al. |
| 9,487,893 B2 | 11/2016 | Moore et al. |
| 9,539,365 B2 | 1/2017 | Kasuga et al. |
| 9,572,909 B2 | 2/2017 | Simpson et al. |
| 9,585,666 B2 | 3/2017 | Yu et al. |
| 9,737,632 B2 | 8/2017 | Johnson et al. |
| 9,884,027 B2 | 2/2018 | Johnson |
| 9,938,373 B2 | 4/2018 | Wang et al. |
| 10,016,464 B2 | 7/2018 | Murphy et al. |
| 10,080,687 B2 | 9/2018 | Macewan |
| 10,124,089 B2 | 11/2018 | MacEwan |
| 10,149,749 B2 | 12/2018 | Macewan et al. |
| 10,166,315 B2 | 1/2019 | Johnson et al. |
| 10,227,568 B2 | 3/2019 | Johnson |
| 10,231,821 B2 | 3/2019 | Gabriele et al. |
| 10,233,427 B2 | 3/2019 | Johnson |
| 10,239,262 B2 | 3/2019 | Johnson |
| 10,294,449 B2 | 5/2019 | Johnson |
| 10,335,154 B2 | 7/2019 | Johnson et al. |
| 10,363,041 B2 | 7/2019 | Yu et al. |
| 10,381,672 B2 | 8/2019 | Lee et al. |
| 10,405,963 B2 | 9/2019 | Mcalpine et al. |
| 10,406,346 B2 | 9/2019 | Scott-Carnell et al. |
| 10,413,574 B2 | 9/2019 | Fong et al. |
| 10,420,856 B2 | 9/2019 | Arinzeh et al. |
| 10,441,403 B1 | 10/2019 | MacEwan et al. |
| 10,441,685 B2 | 10/2019 | MacEwan |
| 10,588,734 B2 | 3/2020 | MacEwan et al. |
| 10,617,512 B2 | 4/2020 | MacEwan et al. |
| 10,632,228 B2 | 4/2020 | MacEwan |
| 10,682,444 B2 | 6/2020 | MacEwan |
| 10,738,152 B2 | 8/2020 | Wang et al. |
| 10,888,409 B2 | 1/2021 | MacEwan et al. |
| 11,000,358 B2 | 5/2021 | MacEwan et al. |
| 11,071,617 B2 | 7/2021 | MacEwan et al. |
| 11,096,772 B1 | 8/2021 | MacEwan et al. |
| 11,173,234 B2 | 11/2021 | MacEwan |
| 11,176,234 B2 | 11/2021 | Andersson et al. |
| 11,224,677 B2 | 1/2022 | MacEwan |
| 11,253,635 B2 | 2/2022 | MacEwan |
| 11,311,366 B2 | 4/2022 | MacEwan et al. |
| 11,471,260 B2 | 10/2022 | MacEwan et al. |
| 11,596,717 B2 | 3/2023 | MacEwan |
| 11,826,487 B2 | 11/2023 | MacEwan |
| 2002/0081732 A1 | 6/2002 | Bowlin et al. |
| 2002/0090725 A1 | 7/2002 | Simpson et al. |
| 2002/0173213 A1 | 11/2002 | Chu et al. |
| 2002/0192251 A1 | 12/2002 | Collin |
| 2003/0004579 A1 | 1/2003 | Rousseau et al. |
| 2003/0054035 A1 | 3/2003 | Chu et al. |
| 2004/0013819 A1 | 1/2004 | Hou et al. |
| 2004/0018226 A1 | 1/2004 | Wnek et al. |
| 2004/0037813 A1 | 2/2004 | Simpson et al. |
| 2004/0096532 A1 | 5/2004 | Dubson et al. |
| 2004/0102614 A1 | 5/2004 | Islam et al. |
| 2005/0104258 A1 | 5/2005 | Lennhoff |
| 2005/0167311 A1 | 8/2005 | Tonsfeldt et al. |
| 2005/0222591 A1 | 10/2005 | Gingras et al. |
| 2005/0233021 A1 | 10/2005 | Chun et al. |
| 2006/0014460 A1 | 1/2006 | Alexander et al. |
| 2006/0085063 A1 | 4/2006 | Shastri et al. |
| 2006/0094320 A1 | 5/2006 | Chen et al. |
| 2006/0153904 A1 | 7/2006 | Smith et al. |
| 2006/0193578 A1 | 8/2006 | Ouderkirk et al. |
| 2006/0204539 A1 | 9/2006 | Atala et al. |
| 2006/0240110 A1 | 10/2006 | Kiick et al. |
| 2006/0246798 A1 | 11/2006 | Reneker et al. |
| 2006/0263417 A1 | 11/2006 | Lelkes et al. |
| 2006/0264140 A1 | 11/2006 | Andrady et al. |
| 2007/0073344 A1 | 3/2007 | Jahns et al. |
| 2007/0152378 A1 | 7/2007 | Kim |
| 2007/0155273 A1 | 7/2007 | Chu et al. |
| 2007/0225631 A1 | 9/2007 | Bowlin et al. |
| 2007/0269481 A1 | 11/2007 | Li et al. |
| 2008/0065123 A1 | 3/2008 | Yli-Urpo et al. |
| 2008/0102145 A1 | 5/2008 | Kim et al. |
| 2008/0112998 A1 | 5/2008 | Wang |
| 2008/0207798 A1 | 8/2008 | Hellring et al. |
| 2008/0208358 A1 | 8/2008 | Bellamkonda et al. |
| 2008/0220042 A1 | 9/2008 | Hashi et al. |
| 2008/0237934 A1 | 10/2008 | Reneker et al. |
| 2009/0028921 A1 | 1/2009 | Arinzeh |
| 2009/0074832 A1 | 3/2009 | Zussman et al. |
| 2009/0075354 A1 | 3/2009 | Reneker et al. |
| 2009/0155326 A1 | 6/2009 | Mack et al. |

(56) References Cited

U.S. PATENT DOCUMENTS

| | | |
|---|---|---|
| 2009/0162468 A1 | 6/2009 | Barinov et al. |
| 2009/0171467 A1 | 7/2009 | Mann et al. |
| 2009/0202616 A1 | 8/2009 | Chong et al. |
| 2009/0214614 A1 | 8/2009 | Everland et al. |
| 2009/0228021 A1 | 9/2009 | Leung |
| 2009/0246259 A1 | 10/2009 | Kita et al. |
| 2009/0317446 A1 | 12/2009 | Tan et al. |
| 2010/0003305 A1 | 1/2010 | Pattanaik |
| 2010/0047309 A1 | 2/2010 | Lu et al. |
| 2010/0061962 A1 | 3/2010 | Li |
| 2010/0076377 A1 | 3/2010 | Ehrenreich et al. |
| 2010/0092687 A1 | 4/2010 | Sumida et al. |
| 2010/0093093 A1 | 4/2010 | Leong et al. |
| 2010/0119564 A1 | 5/2010 | Kasuga et al. |
| 2010/0120115 A1 | 5/2010 | Ogle et al. |
| 2010/0137902 A1 | 6/2010 | Lee et al. |
| 2010/0166854 A1 | 7/2010 | Michniak-Kohn et al. |
| 2010/0174368 A1 | 7/2010 | Lynch et al. |
| 2010/0179659 A1 | 7/2010 | Li et al. |
| 2010/0185219 A1 | 7/2010 | Gertzman et al. |
| 2010/0190254 A1 | 7/2010 | Chian et al. |
| 2010/0233115 A1 | 9/2010 | Patel et al. |
| 2010/0273258 A1 | 10/2010 | Lannutti et al. |
| 2010/0291182 A1 | 11/2010 | Palasis et al. |
| 2010/0292791 A1 | 11/2010 | Lu et al. |
| 2010/0297208 A1 | 11/2010 | Fry et al. |
| 2010/0330419 A1 | 12/2010 | Cui et al. |
| 2010/0330423 A1 | 12/2010 | Cui et al. |
| 2010/0331980 A1 | 12/2010 | Lee et al. |
| 2011/0014289 A1 | 1/2011 | Datta et al. |
| 2011/0087277 A1 | 4/2011 | Mola et al. |
| 2011/0098826 A1 | 4/2011 | Mauck et al. |
| 2011/0101571 A1 | 5/2011 | Reneker |
| 2011/0111012 A1 | 5/2011 | Pepper et al. |
| 2011/0150973 A1 | 6/2011 | Bowlin et al. |
| 2011/0152897 A1 | 6/2011 | Bates |
| 2011/0174158 A1 | 7/2011 | Walls et al. |
| 2011/0180951 A1 | 7/2011 | Teo et al. |
| 2011/0242310 A1 | 10/2011 | Beebe et al. |
| 2011/0280919 A1 | 11/2011 | Moloye-Olabisi et al. |
| 2011/0287082 A1 | 11/2011 | Smith et al. |
| 2012/0015331 A1 | 1/2012 | Wood et al. |
| 2012/0029654 A1 | 2/2012 | Xu et al. |
| 2012/0040581 A1 | 2/2012 | Kim |
| 2012/0123342 A1 | 5/2012 | Andrews et al. |
| 2012/0165957 A1 | 6/2012 | Everland et al. |
| 2012/0221025 A1 | 8/2012 | Simpson et al. |
| 2012/0225039 A1 | 9/2012 | Li et al. |
| 2012/0265300 A1 | 10/2012 | Mauck et al. |
| 2012/0301567 A1 | 11/2012 | Pokorny et al. |
| 2012/0310260 A1 | 12/2012 | Hamlin et al. |
| 2012/0330437 A1 | 12/2012 | El-Kurdi et al. |
| 2013/0030548 A1* | 1/2013 | Ling ............... C12M 21/08 435/395 |
| 2013/0035704 A1 | 2/2013 | Dudai |
| 2013/0040140 A1 | 2/2013 | Joo et al. |
| 2013/0110138 A1 | 5/2013 | Hurtado et al. |
| 2013/0115457 A1 | 5/2013 | Haynie et al. |
| 2013/0144249 A1 | 6/2013 | Fenton et al. |
| 2013/0197663 A1 | 8/2013 | Macewan et al. |
| 2013/0251762 A1 | 9/2013 | Wei et al. |
| 2013/0338791 A1 | 12/2013 | McCullen et al. |
| 2014/0004159 A1 | 1/2014 | Xie et al. |
| 2014/0030315 A1 | 1/2014 | Johnson |
| 2014/0081297 A1 | 3/2014 | Hoke et al. |
| 2014/0128345 A1 | 5/2014 | Woodrow et al. |
| 2014/0272225 A1 | 9/2014 | Johnson |
| 2014/0288663 A1 | 9/2014 | Borden et al. |
| 2014/0303727 A1 | 10/2014 | Atlas et al. |
| 2014/0322512 A1 | 10/2014 | Pham et al. |
| 2015/0030659 A1 | 1/2015 | Langer et al. |
| 2015/0045818 A1 | 2/2015 | Kim et al. |
| 2015/0132423 A1 | 5/2015 | Johnson |
| 2015/0133454 A1 | 5/2015 | Choy et al. |
| 2015/0190285 A1 | 7/2015 | MacEwan |
| 2015/0250927 A1 | 9/2015 | MacEwan |
| 2015/0297791 A1 | 10/2015 | Patel et al. |
| 2015/0342719 A1 | 12/2015 | Chen et al. |
| 2016/0022873 A1 | 1/2016 | Besner et al. |
| 2016/0083692 A1 | 3/2016 | Hardy et al. |
| 2016/0083868 A1 | 3/2016 | Park |
| 2016/0136330 A1 | 5/2016 | Benkirane-Jessel et al. |
| 2016/0302869 A1 | 10/2016 | Chopra |
| 2016/0317706 A1 | 11/2016 | Johnson |
| 2017/0095591 A1 | 4/2017 | Zuhaib et al. |
| 2017/0119886 A1 | 5/2017 | Johnson et al. |
| 2017/0182206 A1 | 6/2017 | Johnson et al. |
| 2017/0182211 A1 | 6/2017 | Raxworthy et al. |
| 2017/0203004 A1 | 7/2017 | Murphy et al. |
| 2017/0319323 A1* | 11/2017 | MacEwan ............... A61L 27/14 |
| 2017/0319742 A1 | 11/2017 | Johnson et al. |
| 2017/0326270 A1* | 11/2017 | MacEwan ............... A61L 27/26 |
| 2018/0116973 A1 | 5/2018 | Johnson |
| 2018/0161185 A1 | 6/2018 | Kresslein et al. |
| 2018/0174367 A1 | 6/2018 | Marom et al. |
| 2018/0221537 A1 | 8/2018 | Johnson et al. |
| 2018/0237952 A1 | 8/2018 | Johnson et al. |
| 2018/0245243 A1 | 8/2018 | Krieger et al. |
| 2018/0263919 A1 | 9/2018 | Hoke et al. |
| 2018/0368917 A1 | 12/2018 | Dekel et al. |
| 2019/0015563 A1 | 1/2019 | MacEwan |
| 2019/0021837 A1 | 1/2019 | MacEwan et al. |
| 2019/0046692 A1 | 2/2019 | Shefi et al. |
| 2019/0054036 A1 | 2/2019 | Johnson et al. |
| 2019/0102880 A1 | 4/2019 | Parpara et al. |
| 2019/0105128 A1 | 4/2019 | Velazquez et al. |
| 2019/0117774 A1 | 4/2019 | Kasuga et al. |
| 2019/0134267 A1 | 5/2019 | Francis et al. |
| 2019/0134570 A1 | 5/2019 | Pintauro et al. |
| 2019/0153398 A1 | 5/2019 | Johnson |
| 2019/0175786 A1 | 6/2019 | Cohen et al. |
| 2019/0249127 A1 | 8/2019 | Johnson |
| 2019/0269829 A1 | 9/2019 | Johnson et al. |
| 2019/0271098 A1 | 9/2019 | Johnson et al. |
| 2019/0282351 A1* | 9/2019 | Mathisen ............... A61F 2/0077 |
| 2019/0328393 A1 | 10/2019 | Yu et al. |
| 2019/0330419 A1 | 10/2019 | Song et al. |
| 2019/0350688 A1 | 11/2019 | Hurtado et al. |
| 2019/0365520 A1 | 12/2019 | MacEwan et al. |
| 2019/0365958 A1 | 12/2019 | MacEwan |
| 2019/0374227 A1 | 12/2019 | Johnson et al. |
| 2020/0000570 A1 | 1/2020 | MacEwan et al. |
| 2020/0046883 A1 | 2/2020 | Martin et al. |
| 2020/0060800 A1 | 2/2020 | MacEwan et al. |
| 2020/0197153 A1 | 6/2020 | MacEwan et al. |
| 2020/0229679 A1 | 7/2020 | Zhao et al. |
| 2020/0242767 A1 | 7/2020 | Zhao et al. |
| 2020/0277711 A1 | 9/2020 | Xie |
| 2020/0324021 A1 | 10/2020 | Van et al. |
| 2020/0376170 A1 | 12/2020 | Ahn et al. |
| 2020/0390932 A1 | 12/2020 | MacEwan |
| 2021/0001014 A1 | 1/2021 | MacEwan |
| 2021/0030525 A1 | 2/2021 | MacEwan et al. |
| 2021/0052362 A1 | 2/2021 | MacEwan et al. |
| 2021/0128792 A1 | 5/2021 | Dunbar et al. |
| 2021/0228782 A1 | 7/2021 | MacEwan |
| 2021/0236691 A1 | 8/2021 | MacEwan |
| 2021/0267746 A1 | 9/2021 | MacEwan et al. |
| 2021/0338408 A1 | 11/2021 | MacEwan et al. |
| 2021/0353834 A1 | 11/2021 | MacEwan |
| 2022/0175510 A1 | 6/2022 | MacEwan et al. |
| 2022/0249743 A1 | 8/2022 | MacEwan |
| 2023/0030107 A1 | 2/2023 | MacEwan et al. |
| 2023/0033599 A1 | 2/2023 | MacEwan et al. |
| 2023/0074964 A1 | 3/2023 | MacEwan et al. |

FOREIGN PATENT DOCUMENTS

| | | |
|---|---|---|
| AU | 2017232208 A1 | 10/2017 |
| CA | 2094908 A1 | 6/1992 |
| CA | 2386810 A1 | 4/2001 |
| CA | 2802482 A1 | 12/2011 |
| CN | 1994476 A | 7/2007 |
| CN | 102260963 A | 11/2011 |

(56) References Cited

FOREIGN PATENT DOCUMENTS

| | | |
|---|---|---|
| CN | 102691176 A | 9/2012 |
| CN | 103599562 A | 2/2014 |
| CN | 104894750 A | 9/2015 |
| CN | 105455923 A | 4/2016 |
| DE | 102014107826 A1 | 12/2014 |
| EP | 0266035 A1 | 5/1988 |
| EP | 0314109 A2 | 5/1989 |
| EP | 0223374 B1 | 8/1990 |
| EP | 0515522 A1 | 12/1992 |
| EP | 0571415 A1 | 12/1993 |
| EP | 0757127 A1 | 2/1997 |
| EP | 2045375 A1 | 4/2009 |
| EP | 2358301 A1 | 8/2011 |
| EP | 2599858 A2 | 6/2013 |
| EP | 2897561 A1 | 7/2015 |
| EP | 2582868 B1 | 3/2018 |
| EP | 3508641 A1 | 7/2019 |
| EP | 3741896 A1 | 11/2020 |
| EP | 3824853 A1 | 5/2021 |
| GB | 1286858 A | 8/1972 |
| GB | 2181207 A | 4/1987 |
| GB | 2195251 A | 4/1988 |
| JP | 03-161563 A | 7/1991 |
| JP | 3487722 B2 | 1/2004 |
| JP | 2005-534828 A | 11/2005 |
| JP | 2006-283241 A | 10/2006 |
| JP | 2006-328562 A | 12/2006 |
| JP | 2007-303021 A | 11/2007 |
| JP | 2007-303031 A | 11/2007 |
| JP | 2008-223186 A | 9/2008 |
| JP | 2009-061109 A | 3/2009 |
| JP | 2011-059786 A | 3/2011 |
| JP | 2011-509786 A | 3/2011 |
| JP | 4769871 B2 | 9/2011 |
| JP | 4979264 B2 | 7/2012 |
| JP | 2012-528464 A | 11/2012 |
| JP | 2013-518996 A | 5/2013 |
| JP | 2013-534979 A | 9/2013 |
| JP | 5424561 B2 | 2/2014 |
| JP | 6295258 B2 | 3/2018 |
| JP | 6328672 B2 | 5/2018 |
| KR | 10-0439871 B1 | 7/2004 |
| KR | 10-2006-0118937 A | 11/2006 |
| KR | 10-2007-0047873 A | 5/2007 |
| KR | 10-1703095 B1 | 2/2017 |
| SG | 186379 A1 | 1/2013 |
| SG | 11201502207W A | 4/2015 |
| WO | 91/01695 A1 | 2/1991 |
| WO | 01/26610 A1 | 4/2001 |
| WO | 01/27365 A1 | 4/2001 |
| WO | 02/00149 A1 | 1/2002 |
| WO | 2004/016839 A1 | 2/2004 |
| WO | 2006/096791 A2 | 9/2006 |
| WO | 2006/123858 A1 | 11/2006 |
| WO | 2007/086910 A2 | 8/2007 |
| WO | 2008/069760 A1 | 6/2008 |
| WO | 2009/093023 A2 | 7/2009 |
| WO | 2010/041944 A1 | 4/2010 |
| WO | 2010/042651 A1 | 4/2010 |
| WO | 2010/062297 A1 | 6/2010 |
| WO | 2010/112564 A1 | 10/2010 |
| WO | 2010/138619 A2 | 12/2010 |
| WO | 2011/095141 A1 | 8/2011 |
| WO | 2011/106822 A1 | 9/2011 |
| WO | 2011/159889 A2 | 12/2011 |
| WO | 2012/080706 A2 | 6/2012 |
| WO | 2013/025819 A2 | 2/2013 |
| WO | 2013/050428 A1 | 4/2013 |
| WO | 2013/078051 A1 | 5/2013 |
| WO | 2013/106822 A1 | 7/2013 |
| WO | 2014/031721 A1 | 2/2014 |
| WO | 2014/046669 A1 | 3/2014 |
| WO | 2014/145864 A1 | 9/2014 |
| WO | 2014/152906 A2 | 9/2014 |
| WO | 2015/040554 A1 | 3/2015 |
| WO | 2015/048224 A1 | 4/2015 |
| WO | 2015/116917 A1 | 8/2015 |
| WO | 2015/153011 A1 | 10/2015 |
| WO | 2015/157485 A1 | 10/2015 |
| WO | 2016/176559 A1 | 11/2016 |
| WO | 2017/024263 A1 | 2/2017 |
| WO | 2017/035500 A1 | 3/2017 |
| WO | 2017/044982 A1 | 3/2017 |
| WO | 2017/079328 A1 | 5/2017 |
| WO | 2017/196325 A1 | 11/2017 |
| WO | 2018/112203 A1 | 6/2018 |
| WO | 2018/144858 A1 | 8/2018 |
| WO | 2023/007443 A2 | 2/2023 |
| WO | 2023/007444 A1 | 2/2023 |

OTHER PUBLICATIONS

Joint Appendix to Claim Construction Brief filed Jul. 29, 2022, Document 121, in Case No. 1:20-CV- 00980-CFC-JLH, *Acera Surgical, Inc., Retectix, LLC, and Washington University, Plaintiffs, v. Nanofiber Solutions, LLC, Paragen Technologies LLC, Atreon Orthopedics LLC, and Renovoderm LLC, Defendants, and Related Counterclaims*, in 731 paqes.

Joint Appendix to Claim Construction Brief filed Mar. 31, 2023, in Case No. 1:20-cv-00980-CFC-JLH, Document 192, *Acera Surgical, Inc., Retectix, LLC, and Washington University, Plaintiffs, v. Nanofiber Solutions, LLC, Paragen Technologies LLC, Atreon Orthopedics LLC, and Renovoderm LLC, Defendants, and Related Counterclaims* (898 pages). Submitted in 6 parts.

Joint Claim Construction Brief Regarding U.S. Pat. No. 11,224,677, filed Mar. 31, 2023, in Case No. 1:20-cv-00980-FCF-JLH, Document 191, *Acera Surgical, Inc., Retectix, LLC, and Washington University, Plaintiffs v. Nanofiber Solutions, LLC, Paragen Technologies LLC, Atreon Orthopedics LLC, and Renovoderm LLC, Defendants, and Related Counterclaims* (86 pages).

Joint Claim Construction Brief, filed Jul. 29, 2022, in Case No. 1:20-cv-00980-CFC-JLH, Document 120, *Acera Surgical, Inc., Retectix, LLC, and Washington University, Plaintiffs, v. Nanofiber Solutions, LLC, Paragen Technologies LLC, Atreon Orthopedics LLC, and Renovoderm LLC, Defendants, and Related Counterclaims*, in 79 pages.

Joint Claim Construction Chart filed Feb. 7, 2023, Document 172, in Case No. 1:20-CV-00980-CFC-JLH, *Acera Surgical, Inc., Retectix, LLC, and Washington University, Plaintiffs, v. Nanofiber Solutions, LLC, Paragen Technologies LLC, Atreon Orthopedics LLC, and Renovoderm LLC, Defendants, and Related Counterclaims*, in 57 paqes.

Joint Claim Construction Chart, filed Mar. 30, 2023, in Case No. 1:20-cv-00980-CFC-JLH, Document 188, *Acera Surgical Inc., Retectix LLC, and Washington University, Plantiffs, v. Nanofiber Solutions, LLCParagen Technologies LLC, Atreon Orthopedics LLC, and Renovoderm LLC, Defendants, and Related Counterclaims* (39 pages).

Joint Claim Construction Chart, filed May 10, 2022, Document 99, in Case No. 1:20-CV-00980-CFC-JLH, *Acera Surgical, Inc., Retectix, LLC, and Washington University, Plaintiffs, v. Nanofiber Solutions, LLC, Paragen Technologies LLC, Atreon Orthopedics LLC, and Renovoderm LLC, Defendants, and Related Counterclaims*, in 273 pages.

Ju et al., "Bilayered scaffold for engineering cellularized blood vessels," Biomaterials, 31(15): 4313- 4321 (2010).

Kenawy et al., "Release of tetracycline hydrochloride from electrospun poly(ethylene-co-vinylacetate), poly(lactic acid), and a blend," Journal of Controlled Release, 81(1-2): 57-64 (2002).

Khil et al., "Novel Fabricated Matrix Via Electrospinning for Tissue Engineering," Journal of Biomedical Materials Research, Part B, Applied Biomaterials, 72B(1): 117-124 (2004), https://doi.org/10.1002/jbm.b.30122.

Kidoaki et al., "Mesoscopic spatial designs of nano- and microfiber meshes for tissue-engineering matrix and scaffold based on newly devised multilayering and mixing electrospinning techniques," Biomaterials 26: 37-46 (2005), doi: 10.1016/j.biomaterials.2004.01.063.

(56) References Cited

OTHER PUBLICATIONS

Kim et al., "Controlled design of aligned and random nanofibers for 30 bi-functionalized nerve conduits fabricated via a novel electrospinning set-up", Sci Rep vol. 6:23761 (2016).
Kumar et al., "Nanofibers: Effective Generation by Electrospinning and Their Applications," Journal of Nanoscience and Nanotechnology, 12(1): 1-25 (2012).
Le et al., "Engineering a Biocompatible Scaffold with Either Micrometre or Nanometre Scale Surface Topography for Promoting Protein Adsorption and Cellular Response," International Journal of Biomaterials, 2013: 1-16 (2013).
Lee et al., "Development of a composite vascular scaffolding system that withstands physiological vascular conditions," Biomaterials, 29(19): 2891-2898 (2008).
Li et al., "Direct Fabrication of Composite and Ceramic Hollow Nanofibers by Electrospinning" Nano Letters, 4(5) 933-938 (2004).
Li et al., "Electrospinning ofNanofibers: Reinventing the Wheel?" Advanced Materials, 16(14): 1151-1170 (2004).
Li, et al., "Electrospinning Nanofibers as Uniaxially Aligned Arrays and Layer-by-Layer Stacked Films" Advanced Materials, 16(4): 361-366 (2004).
Li, et al., "Electrospinning of Polymeric and Ceramic i"Janofibers as 20 Uniaxiaily Aligned Arrays Nano Lett. 2003, 3, 1167-1171.
Liu et al., "Electrospun Fibrous Mats on Lithographically Micropatterned Collectors to Contra! Celluiar Behaviors," Langmuir 28:"17134-17142 (2012), doi: "10.1021/la30-1490x).
Liu et al., "Tensile Mechanics of Electrospun Multiwalled Nanotube/Poly(methyl methacrylate) Nanofibers," Advanced Materials, 19(9): 1228-1233 (2007).
MacEwan et al., "What makes the optimal wound healing material? A review of current science and introduction of a synthetic nanofabricated wound care scaffold", Cureus, vol. 9(10): 1-12 (2017).
Madhugiri et al., "Electrospun MEH-PPV/SBA-15 Composite Nanofibers Using a Dual Syringe Method," J. American Chemical Society, 125(47): 14531-14538 (2003).
Manavitehrani et al., "Biomedical Applications of Biodegradable Polyesters," Polymers, 8(1): Article 20, 32 pages (2016).
Martinez-Lage, et al., Accidental transmission of Creutzfeldt-Jakob disease by dural cadaveric grafts, Journal of Neurology, Neurosurgery, and Psychiatry, 1994, vol. 57, pp. 1091-1094.
McClure et al., "The use of air-flow impedance to control fiber deposition patterns during electrospinning," Biomaterials, 33(3): 771-779 (2012).
McMillan et al. "Small diameter poro poly (c-caprolactone) films enhance adhesion and growth of human cultured epidermal keratinocyte and dermal fibroblast cells," Tissue Engineering, 13(4): 789-798 (2007).
Merriam-Webster "FIBER" Definition downloaded from h,tps//www.rnerriam web te1.com/dicttonatv/fiber on Jul. 11, 21.
Mi et al. "Asymmetric chitosan membranes prepared by dry/west phase separation: a new type of wound dressing for controlled antibacterial release", Journal of Membrane Science, (vol. 212) pp. 237-254.
Murthy, N. et al., "Biodegradation of Polymers," Polymer Science: A Comprehensive Reference, 9: 547-560 (2012).
Norris et al., "Electrostatic Fabrication of Ultrafine Conducting Fibers: Polyaniline/Polyethylene Oxide Blends" Synthetic Metals 114(2): 109-114 (2000).
Notice of Reasons for Refusal received for Japanese Patent Application No. 2013-515511, mailed on Oct. 28, 2014, 4 pages (2 pages of English Translation and 2 pages of Original Document).
Notice of Reasons for Refusal received for Japanese Patent Application No. 2015-53302, mailed on Jun. 27, 2017, 9 pages (4 pages of English Translation and 5 pages of Original Document).
Notice of Reasons for Refusal received for Japanese Patent Application No. 2015-533026, mailed on Oct. 18, 2016, 8 pages (4 pages of English Translation and 5 pages of Original Document).
Notice of Reasons for Refusal received for Japanese Patent Application No. 2017-160972, mailed on Jul. 3, 2018, 6 pages (3 pages of English Translation and 3 pages of Original Document).
Notice of Reasons for Refusal received for Japanese Patent Application No. 2017-160972, mailed on Oct. 23, 2018, 6 pages (3 pages of English Translation and 3 pages of Original Document).
Notice of Reasons for Refusal received for Japanese Patent Application No. 2019-016666, mailed on Dec. 3, 2019, 8 pages (4 pages of English Translation and 4 pages of Original Document).
Office Action received for European Application No. 12884789.4, mailed on Aug. 12, 2019, 6 pages.
Office Action received for European Application No. 12884789.4, mailed on Sep. 26, 2018, 5 pages.
Office Action received for European Application No. 20175280.5, mailed on Nov. 20, 2023, 7 pages.
Panseri, S., et al., "Electrospun micro- and nanofiber tubes for functional nervous regeneration in sciatic nerve transections", BMC Biotechnology, vol. 8, Apr. 2008, pp. 1-12.
Park et al., "Apparat for Preparing Electrospun Nanofibers: Designing and Electrospinning process for Nanofiber Fabrication," Polymer International, 56(11): 1361-1366 (2007).
Pepper et al., "Factors Influencing Poor Outcomes in Synthetic Tissue-Engineered Tracheal Replacement" Otolaryngol Head Neck Surg. Sep. 2019; 161 (3): 458-467.
Petition for Inter Partes Review of U.S. Pat. No. 10,632,228, dated May 28, 2021 (91 pages).
Pham et al. "Electrospun poly (£-caprolactone) microfiber and multilayer nanofiber/microfiber scaffold: characterization of scaffolds and measurement of cellular infiltration" , Biomacromolecules 2006, pp. 7, 10, 2796-2805, Pub. Sep. 23, 2006.
Pham et al., "Electrospinning of Polymeric Nanofibers for Tissue Engineering Applications: A Review", Tissue Engineering, 12(5): 1197-1211 (2006).
Plaintiffs Acera Surgical, Inc., Retectix, LLC and Washington University's Objections to the Report and Recommendation [D.I 147} filed Oct. 26, 2022, in Case No. 1:20-CV-00980-CFC-JLH, *Acera Surgical, Inc., Retectix, LLC, and Washington University, Plaintiffs*, v. *Nanofiber Solutions, LLC, Paragen Technologies LLC, Atreon Orthopedics LLC, and Renovoderm LLC, Defendants*, and Related Counterclaims, in 18 pages.
Quan et al., "Aligned fibers enhance nerve guide conduits when bridging peripheral nerve defects focused on early repair stage." Neural Regeneration Research 14(5):p. 903-912, May 2019.
Ramakrishna et al., "Electrospun nanofibers: solving global issues," Materials Today, 9(3): 40-50 (2006).
Report and Recommendation filed May 25, 2023, in Case No. 1:20-cv-00980-CFC-JLH, Document 201, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and *Nanofiber Solutions, LLC, and The Research Foundation for the State University of New York*, Counterclaim Plaintiffs, v. *Acera Surgical, Inc.*, Counterclaim Defendant, in 11 paqes.
Doshi, et al., "Electrospinning Process and Applications of Electrospun Fibers," Journal of Electrostatics, 35: 151-160 (1995).
Dubsky et al., "Nanofibers prepared by needleless electrospinning technology as scaffolds for wound healing," J Mater Sci: Mater Med, DOI 10.1007/s 10856-012-4577-7, Feb. 2012.
Dzenis et al., "Hierarchical nano-/micromaterials based on electrospun polymer fibers: Predictive models for thermomechanical behavior" Journal of Computer-Aided Materials Design, 3: 403-408 (1996).
Dzenis et al., "Polymer Hybrid Nano/Micro Composites," Proceedings of the American Society for Composites Ninth Teclmical Conference, pp. 657-665, 1994.
EP Office Action received for European Application No. 11796426.2, mailed on Jul. 20, 2016, 6 pages.
EP Office Action received for European Application No. 11796426.2, mailed on Nov. 23, 2016, 3 pages.
European Examination Report issued for Application No. 12884789.4 dated Feb. 13, 2018 (5 pages).
European Extended Search Report issued for Application No. 11796426.2, dated Mar. 27, 2014 (6 pages).

(56) References Cited

OTHER PUBLICATIONS

European Office Action issued for Application No. 16901840.5, dated Sep. 10, 2021 (9 pages).
European Partial Search Report issued for Application No. 12884789.4, dated Feb. 29, 2016 (8 pages).
European Search Report and Search Opinion received for European Application No. 16901840.5, mailed on Dec. 2, 2019, 10 pages.
European Search Report and Search Opinion received for European Application No. 18164340.4, mailed on Jun. 6, 2019, 7 pages.
European Search Report and Search Opinion received for European Application No. 20175280.5, mailed on Oct. 9, 2020, 9 pages.
European Search Report and Search Opinion received for European Application No. 20205022.5, mailed on Apr. 23, 2021, 8 pages.
Examination Report issued for for Australian Application No. 2011268321, dated Apr. 17, 2015 (4 pages).
Examination Report issued for Indian Application No. 11141/DELNP/2012, dated Jun. 21, 2018 (7 pages).
Fang et al. "Electrospinning: an advanced nanofiber production technology." In: H. Niu, H. Zhou and H. Wang (Eds.), Energy Harvesting Properties of Electrospun Nanofibers (1st ed. [online], pp. 1-Jan. 1, 44). IOP Publishing Ltd. (2020). https://iopscience.iop.org/book/978-0-7503-2005-4/chapter/bk978-0-7503-2005-4ch1 (Accessed Apr. 6, 2021), doi 10.1088/978-0-7503-2005-4ch1.
Figallo et al., "Micropatterned biopolymer 3D scaffold for static and dynamic culture of human fibroblasts," Biotechnology Progress, 23(1): 210-216 (2007).
Foy, et al., Allergic reaction to a bovine dural substitute following spinal cord untethering. Case report, Journal of Neurosurgery Pediatrics 2008; vol. 1, pp. 167-169.
Fridrikh et al., "Controlling the Fiber Diameter during Electrospinning," The American Physical Society, 90(14): 144502 (2003).
GCC Examination Report in Application No. GC 2017-33397 dated Apr. 15, 2019 in 4 pages.
Gnavi et al., "The influence of electrospun fibre size on Schwann cell behaviour and axonal outgrowth." Mater Sci Eng C Mater Biol Appl. Mar. 2015;48:620-31.
Grafe et al., "Nanofiber Webs from Electrospinning," Nonwovens in Filtration—Fifth International Conference, Stuttgart, Germany, Mar. 2003 (5 pages).
Herron, Treatment of a Complex Pressure Ulcer Using a Synthetic Hybrid-Scale Fiber Matrix, Apr. 16, 2021, Cureus, vol. 14 iss. 4, pp. 1-4. (Year: 2021).
Hoke, Nanofiber Nerve Guide for Peripheral Nerve Repair and Regeneration, US Army Medical Research and Material Command. (Year: 2014).
Huang et al., "A review on polymer nanofibers by electrospinning and their applications in nanocomposites," Composites Science and Technology 63: 2223-2253 (2003), doi: 10.1016/S0266-3538(03)00178-7.
Huang et al., "Generation of Synthetic Elastin-Mimetic Small Diameter Fibers and Fiber Networks," Macromolecules 33(8): 2989-2997 (2000).
Indian First Examination Report (English translation) for Application No. 2299/DELNP/2015, dated Oct. 24, 2019, 6 pages.
Indian Frist Examination Report for IN Application No. 201817046790, dated Sep. 29, 2021, 6 pages.
Intention to grant received for European Application No. 12884789.4, mailed on May 12, 2020, 7 pages.
Intention to grant received for European Application No. 18164340.4, mailed on Jan. 3, 2020, 6 pages.
Intention to grant received for European Application No. 20205022.5, mailed on Feb. 21, 2023, 6 pages.
Intention to grant received for European Patent Application No. 11796426.2, mailed on Oct. 6, 2017, 6 pages.
Intention to Grant, EP App. No. 16901840.5, May 7, 2024, 6 pages.
International Preliminary Report on Patentability received for PCT Patent Application No. PCT/IB2022/57028, mailed on Feb. 8, 2024, 7 pages.
International Preliminary Report on Patentability received for PCT Patent Application No. PCT/IB2022/57029, mailed on Feb. 8, 2024, 8 pages.
International Preliminary Report on Patentability received for PCT Patent Application No. PCT/US2011/040691, mailed on Jan. 3, 2013, 9 pages.
International Preliminary Report on Patentability received for PCT Patent Application No. PCT/US2012/056548, mailed on Apr. 2, 2015, 10 pages.
International Preliminary Report on Patentability received for PCT Patent Application No. PCT/US2016/032001, mailed on Nov. 22, 2018, 7 pages.
International Preliminary Report on Patentability received for PCT Patent Application No. PCT/US2022/75995, mailed on Mar. 21, 2024, 15 pages.
International Search Report and Written Opinion received for PCT Patent Application No. PCT/IB2022/057028, mailed on Jan. 6, 2023, 9 pages.
International Search Report and Written Opinion received for PCT Patent Application No. PCT/IB22/57029, mailed on Oct. 18, 2022, 8 pages.
International Search Report and Written Opinion received for PCT Patent Application No. PCT/US2011/040691, mailed on Feb. 24, 2012, 12 pages.
International Search Report and Written Opinion received for PCT Patent Application No. PCT/US2012/056548, mailed on Apr. 26, 2013, 12 pages.
International Search Report and Written Opinion received for PCT Patent Application No. PCT/US2016/032001, mailed on Aug. 11, 2016, 2 pages.
International Search Report and Written Opinion received for PCT Patent Application No. PCT/US22/75995, mailed on Feb. 3, 2023, 18 pages.
Invitation to Pay Additional Fees received for PCT Patent Application No. PCT/US22/75995, mailed on Nov. 15, 2022, 3 pages.
Jaeger et al., "Electrospinning of Ultra-Thin Polymer Fibers," Macromolecular Symposia, 127(1): 141- 150 (1998).
Japanese Office Action Summary issued for Application No. 2015-533026, dated Oct. 18, 2016 (5 pages).
Japanese Office Action translation issued for Application No. 2015-533026, dated Jun. 27, 2017 (4 pages).
3rd International Conference on Electrospinning Conference Program dated Aug. 4-7, 2004, www.ceramics.org/elcetrospin2014.
ASTM International, "Standard Guide for Assessing Microstructure of Polymeric Scaffolds for Use in Tissue-Engineered Medical Products" dated Mar. 27, 2013.
ASTM Standard F2450-10, "Guide for Assessing Microstructure of Polymeric Scaffolds for Use in Tissue- Engineered Medical Products" ASTM International, West Conshohocken, PA, 10 pages (Mar. 27, 2013).
Australian Examination Report No. 1 issued for Application No. 2012390291 dated May 31, 2017 (4 pages).
Australian Examination Report No. 1 issued for Application No. 2016406314 dated Oct. 29, 2020 (4 pages).
Australian Examination Report No. 1 issued for Application No. 2017232208, dated Jan. 8, 2018 (4 pages).
Australian Examination Report No. 2 issued for Application No. 2016406314 dated Mar. 12, 2021 (3 pages).
Australian Examination Report No. 3 issued for Application No. 2016406314 dated Jul. 5, 2021 (4 pages).
Barbol T, et al., Biocompalibility evaluation of dura maTer substitutes in an animal model. Neurological research 2001; vol. 23, pp. 813-820.
Beachley et al., "Polymer nanofibrous structures: Fabrication, biofunctionalization, and cell interactions," Progress in Polymer Science, 35(7): 868-892 (2010).
Beheshtkhoo et al. "Fabrication and Properties of Collagen and Polyurethane Polymeric Nanofibers Using Electrospinning Techniques" Journal of Environmental Treatment Techniques 2019, vol. 7, Issue 4, pp. 802-807.
Bhatt Arai et al. "Electrospun chitosa-based nanofibers and their cellular compatibility", Biomaterials, 26(31): 6176-6184 (2005).

(56) References Cited

OTHER PUBLICATIONS

Boda et al., Electrospraying Electrospun Nanofiber Segments into InjectableMicrospheres for Potential Cell Delivery, Jul. 11, 2018, ACS Applied Materials & Interfaces, vol. 10, pp. 25069-25079. (Year: 2018).
Bognitzki et al., "Nanostmctured Fibers via Electrospinning," Advanced Materials, 13(1): 70-72 (2001).
Bognitzki et al., "Preparation of Fibers with Nanoscaled fvlorpilologies: Electrospinning of Polmer Blends" Polymer Enginering and Science, June ;2001, vol. 41, No. 6, pp. 982-989.
Boland et al., "Tailoring Tissue Engineering Scaffolds Using Electrostatic Proceedings Techniques: A Study of Poly(Glycolic acid) Electrospinning," Journal of Macromolecular Science, 38(12): 1231-1243 (2001).
Boland et al., "Tissue Engineering Scaffolds," Encyclopedia of Biomaterials and Biomedical Engineering, 2(L-Z): 1630-1638 (2004).
Brazilian Technical Report for related Application No. BR112015006301-2, dated Oct. 15, 2020, 5 pages.
Brazilian Technical Report for related Application No. 112012032169-2, dated Feb. 20, 2019 (4 pages).
Camposeo et al., "Lobal Mechanical Properties of Electrospun Fibers Correlate to Their Internal Nanostructure" Nano Lett. 2013, pp. 13, 5056-5062.
Canadian Examiner's Report issued for Application No. 2,885,682, dated Jun. 4, 2018 (5 pages).
Chakrapani et al., "Electrospinning of Type I Collagen and PCL Nanofibers Using Acetic Acid," J. Applied Polymer Science, 125(4): 3221-3227 (2012); Wiley Online Library, Feb. 1, 2012.
Chen et al., "Electrospun 3D Fibrous Scaffolds for Chronic Wound Repair," Materials, 9(4): 272 (2016).
Chen et al., "Preparation and characterization of coaxial electrospun thermoplastic polyurethane/collagen compound nanofibers for tissue engineering applications," Colloids and Surfaces B: Biointerfaces, 79(2): 315-325 (2010).
Chen et al., "Preparation and Study of TPU/Collagen Complex Nanofiber via Electrospinning," AATCC Review, 10(2): 59-63 (2010).
Cheng et al., "Engineering the Microstructure of Electrospun Fibrous Scaffolds by Microtopography," Biomacromolecules 14:1349-1360 (2013), doi: 10.1021/bm302000n).
China Examiner's Report issued for Application No. 201680087078.9, dated Jan. 20, 2021 with translation in 28 pages.
China Second Office Action for Application No. 201680087078.9 dated Jul. 14, 2021 with translation in 28 pages.
Chinese patent office, "China Office Action," issued in connection with China Patent Application No. 201680087078.9 dated Oct. 21, 2021 (5 pages).
Choi et al., "Formation of interfiber bonding in electrospun poly(etherimide) nanofiber web," Journal of Materials Science, 39(4): 1511-1513 (2004).
Chong et al., "Evaluation of electrospun PCL/gelatin nanofibrous scaffold for wound healing and layered dermal reconstruction," Acta Biomaterialia, 3(3): 321-330 (2007).
Clark et al. "Investigation of the Effects of Cell Seeding on Neotissue Formation in a Tissue Engineered Trachea" J Pediatr Surg. Jan. 2016; 51(1) 49-55.
Cole et al., "A comparative long-term assessment of four soft tissue substitutes," Aesthetic Surgery Journal, 31(6): 674-681 (2011).
Cui et al., "Controlled assembly of poly(vinyl pyrrolidone) fibers through an electric-field-assisted electrospinning method," Applied Physics A, 103(1): 167-172 (2011).
Davis, et al., "A biodegradable campsite artifical tendon," Journal of Materials Science: Materials in Medicine 3,359-364 (1992).
Decision to grant a European patent received for European Patent Application No. 11796426.2, mailed on Mar. 1, 2018, 2 pages.
Decision to Grant a Patent received for Japanese Patent Application No. 2013-515511, mailed on Feb. 17, 2015, 5 pages (2 pages of English Translation and 3 pages of Original Document).
Decision to Grant a Patent received for Japanese Patent Application No. 2015-533026, mailed on Jan. 23, 2018, 5 pages (2 pages of English Translation and 3 pages of Original Document).
Decision to Grant a Patent received for Japanese Patent Application No. 2017-160972, mailed on Jan. 8, 2019, 5 pages (2 pages of English Translation and 3 pages of Original Document).
Decision to Grant a Patent received for Japanese Patent Application No. 2019-016666, mailed on Jun. 2, 2020, 5 pages (2 pages of English Translation and 3 pages of Original Document).
Decision to grant received for European Application No. 12884789.4, mailed on Oct. 8, 2020, 2 pages.
Decision to grant received for European Application No. 18164340.4, mailed on Jul. 9, 2020, 2 pages.
Decision to grant received for European Application No. 20205022.5, mailed on Jun. 29, 2023, 2 pages.
Declaration of Gary E. Wnek, Ph.D. in Support of Petition for Inter Partes Review of U.S. Pat. No. 10,632,228 dated Jan. 2021.
Defendants' Initial Invalidity Contentions in Civil Action No. 20-980-CFC-JLH dated Nov. 4, 2021 (618 pages).
Deitzel et al. "The effect of processing variables on the morphology of electrospun nanofibers and textiles" Polymer 42 (2001) pp. 261-272.
Dempsey et al., "Micropatterning of Electrospun Polyurethane Fibers Through Control of Surface Topography," Macromolecular Materials and Engineering 295: 990-994 (2020), doi: 1_ 0.1002/rname.201000152.
Dhandayuthap Ani et al., "Polymeric Scaffolds in Tissue Engineering Application: A Review," International Journal of Polymer Science, vol. 2011, Article ID 290602, (19 pages).
Diaz et al., "Fabrication of structured micro and nanofibers by coaxial electrospinning" Journal of Physics, Conference Series 127: 1-8 (2008), goi: 10.1088/1742-6596/127/1/012008.
Ding et al., "Fabrication of blend biodegradable nanofibrous nonwoven mats via multi-jet electrospinning," Polymer, 45(6): 1895-1902 (2004).
Report and Recommendation filed Oct. 12, 2022, in Case No. 1:20-cv-00980-CFC-JLH, Document 147, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and *Nanofiber Solutions, LLC, and The Research Foundation for the State University of New York*, Counterclaim Plaintiffs, v. *Acera Suraical, Inc.*, Counterclaim Defendant, in 24 pages.
Request for the Submission of an Opinion received for Korean Patent Application No. 10-2013-7001184, mailed on Apr. 21, 2016, 5 pages (3 pages of English Translation and 2 pages of Original Document).
Request for the Submission of an Opinion received for Korean Patent Application No. 10-2013-7001184, mailed on Sep. 17, 2015, 6 pages (3 pages of English Translation and 3 pages of Original Document).
Request for the Submission of an Opinion received for Korean Patent Application No. 10-2015-7009820, mailed on Nov. 28, 2018, 11 pages (6 pages of English Translation and 5 pages of Original Document).
Request for the Submission of an Opinion received for Korean Patent Application No. 10-2019-7033062, mailed on Dec. 23, 2019, 5 pages of English Translation only.
Rieger et al., "Designing Electrospun Nanofiber Mats to Promote Wound Healing—A Review," J. Matererials Chemistry B, 1(36): 4531-4541 (2013).
Schneider et al. "Influence of pH on Wound-healing: a New Perspective for Wound-therapy" 2007 Arch. Dermatol. Res. 298:413-420.
Search and Examination Report for SG 2012092888, issued Jan. 30, 2015, 8 pgs.
Shin et al. "Experimental characterization of electrospinning: the electrically forced jet and instabilities," Polymer, 42(25): 9955-9967 (2001).
Shin et al., "Electrospun PLGA nanofiber scaffolds for articular cartilage reconstruction: mechanical stability, degradation and cellular responses under mechanical stimulation in vitro," Journal of Biomaterials Science, Polymer Edition, 17(1-2): 103-119 (2006).

(56) References Cited

OTHER PUBLICATIONS

Singapore Examination Report dated for Application No. 11201502207W, dated Jun. 13, 2017 (8 pages).
Singapore Search and Examination Report for SG 2012092888, dated May 15, 2014, 17 pgs.
Smith et al., "Suture-reinforced electrospun polydioxanone-elastin small-diameter tubes for use in vascular tissue engineering: a feasibility study," Acta Biomaterialia 4(1): 58-66 (2008).
Stitzel, J.D et al., "Arterial Smooth Muscle Cell Proliferation on a Novel Biomimicking, Biodegradable Vascular Graft Scaffold," Journal ofBiomaterials Applications 16(1): 22-33 (2001).
Subbiah et al. "Electrospinning of Nanofibers," J. of Applied Polymer Science, 96: 557-569 (2005).
Supplementary European Search Report and Search Opinion received for European Application No. 12884789.4, mailed on Jun. 16, 2016, 12 pages.
Tan et al., "Tensile test of a single nanofiber using an atomic force microscope tip", Applied Physics Letters 86, 073115 (2005).
Technical Report for related Application No. BR112012032169-2, dated Feb. 20, 2019, 4 pages.
Teo et al., "Electrospun scaffold tailored for tissue-specific extracellular matrix," Biotechnology Journal, 1(9): 918-929 (2006).
Thomas et al. "Electrospun bioactive nanocomposite scaffolds of polycaprolactone and nanohydroxyapatite for bone tissue engineering," Journal ofNanoscience Nanotechnology, 6(2): 487-93 (2006).
Tormala, et al., "Ultra-High-Strength absorbable self-reinforeced polyglycolide (SR-PGA) composite rods for internal fixation of bone fractures: In vitro and in vivo study" Journal of Biomedical Materials Research, Jan. 1991.
U.S. Provisional Application filed by Mar. 29, 2015, by Johnson, U.S. Appl. No. 62/154,286.
Valizadeh et al., "Electrospinning and electrospun nanofibres," IET Nanobiotechnol., c:014, vol. 8, Iss. 2, pp. 83-92.
Vaz et al. "Design of scaffold for blood vessel tissue engineering ing a multiple-layering electrospinning technique," Acta Biomaterialia, 1(5): 572-582 (2005).
Wikipedia, "Polyhydroxyethylmethacrylate," downloaded on Dec. 18, 2019 from https://en.wikipedia.org/wiki/Polyhydroxyethylmethacrylate (3 pages).
Wikipedia, hydroxyethylmethacraylte, 3 pages (Year: 2019).
Wise, Histologic proof that acellular dermal matrices (ADM)-Enduragen, DermaMalrix, and DuraMatrix-are not repopulaled or nonviable and that AlloDerm may be repopulated but degraded synchronously. Aesthetic surgery Journal/ the American Society for Aesthetic Plastic surgery, 2012; vol. 32, pp. 355-358.
Written Decision on Registration received for Korean Patent Application No. 10-2013-7001184, mailed on Oct. 28, 2016, 4 pages (2 pages of English Translation and 2 pages of Original Document).
Written Decision on Registration received for Korean Patent Application No. 10-2019-7033062, mailed on Sep. 2, 2020, 4 pages (2 pages of English Translation and 2 pages of Original Document).
Wulkersdorfer et al., "Bimodal Porous Scaffolds by Sequential Electrospinning of Poly(glycolic acid) with Sucrose Particles," International Journal of Polymer Science 2010: 1-9 (2010).
Xie et al., Nerve Guidance Conduits Based on Double-Layered Scaffolds of Electrospun Nanofibers for Repairing the Peripheral Nervous System, ACS Appl Mater Interface; 6(12): 9472-9480. (Year: 2014).
Xie et al. "Radially Aligned Electrospun Nanofibers as Dural Substitutes for Wound Closure and Tissue Regeneration Applicalions," ACS Nano, 4(9): 5027-5036 (2010).
Xie et al., "Putting electrospun nanofibers to work for biomedical research," Macromol Rapid Commun., 29(22): 1775-1792 (2008).
Xie et al., "Neurites outgrowth on nanofiber scaffolds with different orders, structures, and surface properties," ACS Nano, 3(5): 1151-1159 (2009).
Xie, et al., "Conductive core-sheath nanofibers and their potential applications in neural tissue engineering," Adv Funct Mater, 19(14): 2312-2318 (2009).
Xie, et al., Radially Aligned, Electrospun Nanofibers as Dural Substitutes for Wound Closure and Tissue Regeneration Aoolicalion, ACS Nano, 2010, vol. 4, No. 9, pp. 5027-5036.
Xing et al., Multi Material ElectroSpinniing From Methods to Biomedical Applications, Mater. Toda Bio. (Year: 2023).
Yarin, et al., "Taylor Cone and Jetting from Liquid Driplets in Electrospinning of Nanofibers," Journal of Applied Physics, 90(9): 4836-4846 (2001) https://doi.org/10.1063/1.1408260; College of Polymer Science and Polymer Engineering. 85 (2001). https://ideaexchange.uakron.edu/polymer_ideas/85.
Yogeshwar et al., "Electrospinning of Type I Collagen and PCL Nanofibers Using Acetic Acid," Wiley Online Library, Feb. 1, 2012.
Zerris, et al., Repair of the dura mater with processed collagen devices. Journal of biomedical materials research Part B, Applied biomaterials 2007; vol. 83, pp. 580-588.
Zong et al., "Structure and process relationship of electrospun bioabsorbable nanofiber membranes," Polymer, 43(16): 4403-4412 (2002).

* cited by examiner

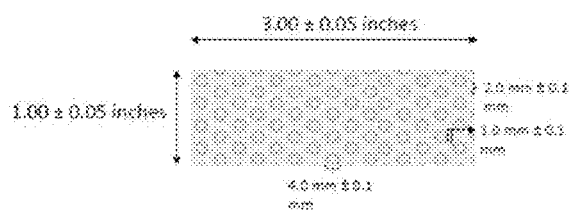
FIG. 12A
FIG. 12C
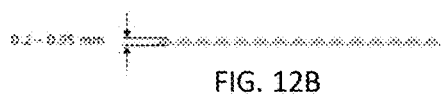
FIG. 12B
FIG. 12D

COMBINED MACRO AND MICRO-POROUS HYBRID-SCALE FIBER MATRIX

FIELD

Embodiments of the disclosure generally related to sheets of a hybrid-scale fiber matrix hybrid-scale fiber matrix having macro and micro pores for improving biocompatibility.

DESCRIPTION

Numerous pathological conditions and surgical procedures result in substantial defects in a variety of organs, tissues, and anatomical structures. In the majority of such cases, surgeons and physicians are required to repair such defects utilizing specialized types of surgical meshes, materials, and/or scaffolds. Unfortunately, the in vivo performance of known surgical materials is negatively impacted by a number of limiting factors. For instance, existing synthetic surgical meshes typically result in excessive fibrosis or scarification leading to poor tissue integration and increased risk of post-operative pain. Simultaneously, known biologic materials may induce strong immune reactions and aberrant tissue ingrowth which negatively impact patient outcomes. Additionally, existing synthetic surgical meshes can create scarification, post-operative pain, limited mobility, limited range of motion, adhesions, infections, erosion, poor biomechanical properties, and/or poor intra-operative handling.

Nanofabricated, nanofiber, or hybrid-scale fiber matrices are meshes or materials composed of reabsorbable polymer fibers tens to thousands of times smaller than individual human cells, which have recently been proposed as a unique substrate for implantable surgical meshes and materials. Generally, existing nanofiber materials tend to possess suboptimal mechanical performance compared to known surgical meshes. Existing nanofiber materials do not possess the tensile strength, tear resistance, and burst strength needed for numerous surgical applications or for basic intraoperative handling prior to in vivo placement. To combat this deficiency, known meshes are formed using higher fiber densities as a means of improving mechanical strength. Yet, utilization of such high-density meshes can decrease effective cellular and tissue ingrowth into the mesh, decrease mesh integration with native tissue, and reduce the biocompatibility of the polymeric implant. As a result, nanofiber or hybrid-scale fiber matrix materials with increased thickness and/or strength and favorable cellular and/or tissue integration and biocompatibility is needed as well as a method for producing nanofiber materials.

Repairs to tissues may be facilitated by one or more materials as described herein, including sheets of polymeric materials or processed tissue that acts like the native tissue in question. For example, skin wounds, including those caused by trauma or deliberately during a medical procedure, may be repaired by application of materials with favorable cellular and tissue integration. To facilitate repair of skin wounds, dressings and other coverings may be applied in both clinical and surgical settings, to promote healing and protect the wound from further harm. Typical wound dressings have a variety of purposes, including absorption of exudate, drainage of exudate, management of exudate, debriding of foreign material and dead cellular matter, stemming bleeding, protecting from infection, and the easing of pain, as well as generally promoting the healing process. As another example, neurosurgical repairs may be effected using one or more materials described herein.

In addition while cell microarrays may be useful in biomedical research and tissue engineering, at least some known techniques for producing such cell microarrays may be costly and time consuming, and may require the use of specialized, sophisticated instrumentation.

SUMMARY

Various embodiments described herein relate to sheets of a hybrid-scale fiber matrix having macro and micro pores for improving biocompatibility.

In particular, in some embodiments, a three-dimensional electrospun hybrid-scale fiber matrix is described for use in repairing tissue for wound care, the three-dimensional hybrid-scale fiber matrix comprises: a flexible electrospun fiber network, the flexible electrospun fiber network comprising: a first set of electrospun fibers comprising a first bioresorbable polymer; and a second set of electrospun fibers comprising a second bioresorbable polymer, wherein the first bioresorbable polymer comprises a different composition from the second bioresorbable polymer; the flexible electrospun fiber network further comprising one or more macro-scale pores and one or more micro-scale pores, the one or more macro-scale pores comprising an opening of about 1 mm to about 20 mm, and the one or more micro-scale pores comprising an opening with areas of about 10 $\mu m^2$ to about 10,000 $\mu m^2$, wherein the three-dimensional electrospun hybrid-scale fiber matrix is sufficiently flexible to facilitate application of the three-dimensional electrospun nanofiber synthetic skin graft to uneven surfaces of the tissue, wherein the three-dimensional electrospun nanofiber synthetic skin graft is sufficiently flexible to enable movement of the three-dimensional electrospun hybrid-scale fiber matrix by the tissue, and wherein the first set of electrospun fibers and the second set of electrospun fibers are configured to degrade after application to the tissue.

In some embodiments of the three-dimensional electrospun hybrid-scale fiber matrix the one or more macro-scale pores of the three-dimensional electrospun hybrid-scale fiber matrix are configured to allow flow through or management of an exudate. In some embodiments of the three-dimensional electrospun hybrid-scale fiber matrix, the one or more micro-scale pores of the three-dimensional electrospun hybrid-scale fiber matrix are configured to facilitate cell growth.

In some embodiments, the three-dimensional electrospun hybrid-scale fiber matrix further comprises at least one projection arising from the surface. In some embodiments, of the three-dimensional electrospun hybrid-scale fiber matrix, the first bioresorbable polymer comprises poly(lactic-co-glycolic acid), and the second bioresorbable polymer comprises polydioxanone. In some embodiments, of the three-dimensional electrospun hybrid-scale fiber matrix, the perforations are distributed equally throughout the matrix.

Also described is a method of manufacturing a biomedical patch device for tissue repair, the method comprising: depositing a first structure of fibers having electrospun nanofibers via electrospinning, the first structure of fibers configured to promote cell growth; and depositing a second structure of fibers having electrospun nanofibers via electrospinning, the second structure of fibers configured to promote cell growth, the first structure of fibers comprising a different composition from the second structure of fibers; the first structure of fibers and the second structure of fibers comprising one or more macro-scale pores and one or more micro-scale pores, the one or more macro-scale pores comprising an opening of about 1 mm to about 20 mm, and the one or more micro-scale pores comprising an opening with areas of about 10 µm² to about 10,000 µm²; the biomedical patch device comprising a surface, wherein the surface comprises a surface pattern configured to contact tissue, wherein the surface pattern, the first structure of fibers, and the second structure of fibers are configured to promote cell growth in one or more defined directions, the biomedical patch device sufficiently flexible to facilitate application of the biomedical patch device to uneven surfaces of the tissue, the biomedical patch device sufficiently flexible to enable movement of the biomedical patch device with the tissue, and wherein the first structure of fibers and the second structure of fibers are configured to degrade after application to the tissue.

In some embodiments of the method, a first portion of the biomedical patch of a particular size comprises a higher number of fibers than a second portion of the biomedical patch of the particular size. In some embodiments of the method, the surface pattern is formed by positioning a mask between a collector and a spinneret, wherein the mask is configured to prevent depositing at least some of the first structure of fibers or the second structure of fibers on the collector. In some embodiments of the method, the surface pattern is formed by depositing the first structure of fibers and the second structure of fibers directly on a collector without a mask. In some embodiments of the method, the surface pattern comprises a plurality of organized features. In some embodiments, the surface pattern comprises a plurality of topographical features configured to further promote migration of cells in one or more of the plurality of defined directions. In some embodiments, the macro-scale pores are generated through cutting, including mechanically, electronically, and/or computer controlled cutting. In some embodiments, the cutting is laser cutting. In some embodiments, the surface pattern further comprises projections arising from the surface. In some embodiments, the surface pattern further comprises indentations projecting below from the surface.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached FIGURES, the invention not being limited to any particular disclosed embodiment(s).

BRIEF DESCRIPTION OF THE DRAWINGS

FIGS. 12A-12D illustrate an embodiment of a macro and micro-porous sheet of hybrid-scale fiber matrix.

DETAILED DESCRIPTION

Figure 1:
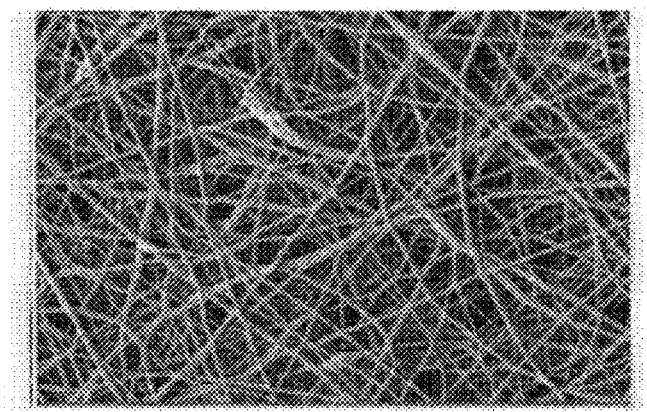
FIG. 1 illustrates a scanning electron micrograph of an embodiment of a non-woven hybrid-scale fiber matrix of the disclosure.

Embodiments provided herein facilitate repairing biological tissue or reinforcing biomedical material based on a biomedical patch (e.g., graft, nanofiber matrix, hybrid-scale fiber matrix, sheet) including a plurality of fibers, such as shown in FIG. 1. Such fibers may have a very small cross-sectional diameter (e.g., from 1-3000 nanometers, from 1-1000 nanometers) and, accordingly, may be referred to as nanofibers and/or microfibers. While biomedical patches are described herein with reference to dura mater and use as a surgical mesh, embodiments described may be applied to any biological tissue. In certain embodiments, the biomedical patches may be used as treatment for skin wounds. Moreover, although described as biomedical patches, structures with fibers may be used for other purposes. Accordingly, embodiments described are not limited to biomedical patches.

Patches may be described in further detail in U.S. Pat. Pub. Nos. 2017/0326270 and 2017/0319323, as well as U.S. Pat. No. 10,124,089, the entirety of each of which is hereby incorporated by reference in their entirety.

Advantageously, embodiments of the disclosed hybrid-scale fiber matrix sheaths can be both micro and macroporous (e.g., meshed). The hybrid-scale fiber matrix itself can be microporous, and additional macro cuts/slits/pores/holes can be added into the matrix to provide an avenue allowing for exudate (e.g., liquids) to pass through the sheet. This can be particularly advantageous for wet wounds, as it can be problematic to have liquids trapped between the sheet and the wound. Excessive exudate buildup in a wound may lead to tissue damage and infection— therefore, adequate drainage and pass through of exudate may improve healing outcomes during wound treatment.

Advantageously, embodiments of the disclosed sheets can include a critical and specific cut pattern to be optimized for both cellular and tissue ingrowth in the material as well as fluid flow. Other physical properties can be optimized as well, such as stretching of the sheet to cover additional surface area strength, flexibility, and overall conformability, in addition to other properties. Further, embodiments of the disclosure can allow for the pattern to be controllable, and thus a user can modify the sheets as desired to optimize different properties.

Generally, the present disclosure is directed to non-woven graft materials including two or more distinct types of fiber compositions, each of which possesses independent mechanical, chemical and/or biological properties. Further, the material is both micro and macroporous. For example, in one embodiment, inclusion of one fiber composition can stabilize the resulting non-woven graft material, while the other fiber composition can improve stability, free-shrinkage properties, mechanical properties, and resorption rate of the non-woven graft material.

As used interchangeably herein, "non-woven graft material" and "non-woven graft fabric" refer to a material having a structure of individual fibers or threads which are interlaid, but not in an identifiable manner as in a knitted or a woven fabric. Non-woven graft materials and non-woven graft fabrics can be formed from many processes such as for example, electrospinning processes, meltblowing processes, spunbonding processes, melt-spraying and bonded carded web processes. The basis weight of non-woven graft materials is usually expressed in ounces of material per square yard (osy) or grams per square meter (gsm) and the fiber diameters are usually expressed in nanometers and micrometers (microns). Suitable basis weight of non-woven graft materials of the present disclosure can range from about 50 gsm to about 300 gsm. More suitably, basis weight of non-woven graft materials of the present disclosure can range from about 70 gsm to about 140 gsm. The tensile strength of the non-woven graft material of the present disclosure can range from about 5 Newtons (N) to about 50 Newtons (N), including from about 1 N to about 10 N to about 15 N. The strength of the non-woven graft material of the present disclosure can also be described in terms of suture pull-out strength, which refers to the force at which a suture can be torn from the non-woven graft material. Suitable suture pull-out strength can range from about 1 N to about 5 N.

As used herein the term "microfibers" refers to small diameter fibers having an average diameter not greater than 75 microns, for example, having an average diameter of from about 0.5 microns to about 50 microns, or more particularly, microfibers having an average diameter of from about 2 microns to about 40 microns. Another frequently used expression of fiber diameter is denier. The diameter of a polypropylene fiber given in microns, for example, may be converted to denier by squaring, and multiplying the result by 0.00629, thus, a 15 micron polypropylene fiber has a denier of about 1.42 (152×0.00629=1.415).

As used herein, the terms "nano-sized fibers" or "nanofibers" refer to very small diameter fibers having an average diameter not greater than 2000 nanometers, not greater than 1500 nanometers, and suitably, not greater than 1000 nanometers (nm). Nanofibers are generally understood to have a fiber diameter range of about 10 to about 1500 nm, more specifically from about 10 to about 1000 nm, more specifically still from about 20 to about 500 nm, and most specifically from about 20 to about 400 nm. Other exemplary ranges include from about 50 to about 500 nm, from about 100 to 500 nm, or about 40 to about 200 nm.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al., the entirety of each of which is hereby incorporated by reference in their entirety.

As used herein the term "meltblown fibers" refers to fibers formed by extruding a molten thermoplastic material through a plurality of fine, usually circular, die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form randomly disbursed meltblown fibers. Such a process is disclosed, for example, in U.S. Pat. No. 3,849,241, which is hereby incorporated by reference in its entirety. Meltblown fibers are microfibers which may be continuous or discontinuous and are generally smaller than 10 microns in diameter.

As used herein, the term "electrospinning" refers to a technology which produces nano-sized fibers referred to as electrospun fibers from a solution using interactions between fluid dynamics and charged surfaces. In general, formation of the electrospun fiber involves providing a solution to an orifice in a body in electric communication with a voltage source, wherein electric forces assist in forming fine fibers that are deposited on a surface that may be grounded or otherwise at a lower voltage than the body. In electrospinning, a polymer solution or melt provided from one or more needles, slots or other orifices is charged to a high voltage relative to a collection grid. Electrical forces overcome surface tension and cause a fine jet of the polymer solution or melt to move towards the grounded or oppositely charged collection grid. The jet can splay into even finer fiber streams before reaching the target and is collected as interconnected small fibers. Specifically, as the solvent is evaporating (in processes using a solvent), this liquid jet is stretched to many times it original length to produce continuous, ultrathin fibers of the polymer. The dried or solidified fibers can have diameters of about 40 nm, or from about 10 to about 100 nm, although 100 to 500 nm fibers are commonly observed. Various forms of electrospun nanofibers include branched nanofibers, tubes, ribbons and split nanofibers, nanofiber yarns, surface-coated nanofibers (e.g., with carbon, metals, etc.), nanofibers produced in a vacuum, and so forth. The production of electrospun fibers is illustrated in many publication and patents, including, for example, P. W. Gibson et al., "Electrospun Fiber Mats: Transport Properties," AIChE Journal, 45(1): 190-195 (January 1999), which is hereby incorporated herein by reference in its entirety.

As used herein, the term "type" such as when referring to "different types of fibers" or "distinct types of fibers" refers to fibers having "a substantially different overall material composition" with measurably different properties, outside of "average diameter" or other "size" differences. That is, two fibers can be of the same "type" as defined herein, yet have different "average diameters" or "average diameter ranges." Although fibers are of different "types" when they have a substantially different overall material composition, they can still have one or more components in common. For example, electrospun fibers made from a polymer blend with a first polymeric component present at a level of at least 10 wt % would be considered a different fiber type relative to electrospun fibers made from a polymer blend that was substantially free of the first polymeric component. Fibers of different "types" can also have a completely different content, each made of a different polymer for example, or one made from a polymer fiber and the other from a titania fiber, or a ceramic fiber and a titania fiber, and so on.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic and atactic symmetries.

Hybrid-Scale Fiber Graft Material

The non-woven graft materials of the present disclosure typically include at least two distinct types of fiber compositions, including compositions comprising hybrid-scale fiber matrices, each of which possesses independent mechanical, chemical and/or biological properties. However, in some embodiments the fibers can be the same. The fiber compositions are suitably made of synthetic resorbable polymeric materials. As used herein, the term "resorbable polymeric material" refers to material formed from resorbable (also referred to as "bioabsorbable") polymers; that is the polymers possess the property to break down when the material is exposed to conditions that are typical of those present in a post-surgical site into degradation products that can be removed from the site within a period that roughly coincides with the period of post-surgical healing. Such degradation products can be absorbed into the body of the patient. The period of post-surgical healing is to be understood to be the period of time measured from the application of the non-woven graft material of the present disclosure to the time that the post-surgical site is substantially healed. This period can range from a period of several days to several months depending on the invasiveness of the surgical and the speed of healing of the particular individual. It is intended that the subject non-woven graft material can be prepared so that the time required for resorption of the non-woven graft material can be controlled to match the time necessary for healing or tissue reformation and regeneration. For example, in some non-woven graft materials of the present disclosure, the fiber compositions are selected to degrade within a period of about one week, while in other non-woven graft materials, the compositions are selected to degrade within a period of three years, or even longer if desired.

The fiber compositions used in the present disclosure can be produced from any resorbable material that meets the criteria of that material as those criteria are described above. The fiber compositions can be formed from resorbable polymers such as (but not limited to) polymers of lactic and glycolic acids, copolymers of lactic and glycolic acids, poly(ether-co-esters), poly(hydroxybutyrate), polycaprolactone, copolymers of lactic acid and ε-aminocapronic acid, lactide polymers, copolymers of poly(hydroxybutyrate) and 3-hydroxyvalerate, polyesters of succinic acid, poly(N-acetyl-D-glucosamine), polydioxanone, cross-linked hyaluronic acid, cross-linked collagen, and the like, and combinations thereof. Suitable synthetic polymers can be, for example, polycaprolactone (poly(ε-caprolactone), PCL), polydioxanone (PDO), poly (glycolic acid) (PGA), poly(L-lactic acid) (PLA), poly(lactid e-co-glycolid e) (PLGA), poly(L-lactide) (PLLA), poly(D,L-lactide) (P(DLLA)), poly (ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly [bis (p-methylphenoxy) phosphazene] (PNmPh), poly(3-hydroxybutyrate-co-3-hydroxyvalerate) (PHBV), poly(ester urethane) urea (PEUU), poly(p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly (ethyleneoxide), poly vinylpyrrolid one; polystyrene (PS) and combinations thereof. Particularly suitable polymers include poly(lactic-co-glycolic acid), polydioxanone, polycaprolactone, and combinations thereof.

The fibers for the fiber compositions may be of a variety of sizes as deemed suitable by one skilled in the art for the end purpose of the non-woven graft material. In some embodiments, the fibers for the fiber composition may be a hybrid-scale fiber matrix. Typically, the fibers of a hybrid-scale fiber matrix have a mean fiber diameter of less than 5 μm, including less than 2 μm, including less than 1.5 μm, and including less than 1.0 μm. For example, in some embodiments, the fibers can have a mean fiber diameter ranging from about 10 nm to about 5 μm, more specifically from about 10 nm to about 1.0 μm, more specifically still from about 20 nm to about 500 nm, and most specifically from about 20 nm to about 400 nm. Other exemplary ranges include from about 50 nm to about 500 nm, from about 100 nm to about 500 nm, and about 40 nm to about 200 nm.

Suitable ratios of the first fiber composition to the second fiber composition resulting in the non-woven graft material can range from about 10 to 1 to about 1 to 10.

In some embodiments, the non-woven graft material is made from a first non-woven fiber composition prepared from poly(lactic-co-glycolic acid) and a second non-woven fiber composition prepared from polydioxanone. The resultant non-woven graft material is a non-biologic tissue substitute designed to provide optimal strength, handling, and suturability, while reducing local inflammation to provide improved wound healing and tissue regeneration. In an exemplary embodiment the non-woven graft material can be synthesized by electrospinning a first fiber composition including a copolymer of glycolide and L-lactide and a second fiber composition including polydioxanone (100 mol %) to create an architecture that is reminiscent of native extracellular matrix. The glycolide mol % to L-lactide mol % can range from about 100 mol % glycolide to 0 mol % L-lactide to 0 mol % glycolide to about 100 mol % L-lactide. A particularly suitable non-woven graft material includes a first fiber composition including a copolymer of glycolide and L-lactide having a glycolide mol % to L-lactide mol % ratio of 90 mol % glycolide and 10 mol % L-lactide. This method of synthesis creates a material that is mechanically strong, while providing the look and feel of native tissue. The architecture of this non-biologic graft material furthermore supports cellular and tissue ingrowth and neoduralization with minimal inflammation.

The non-woven graft material typically can be prepared to be any of a variety of sizes, shapes and thicknesses. Wet and dry non-woven graft material can suitably be cut and trimmed to any desired size and shape. In particularly suitable embodiments, the non-woven graft material has a size ranging from about 0.55 in diameter to about 0.5 in×1 in to about 2.5 cm×2.5 cm (1 in×1 in) to about 25.5 cm×50 cm (10 in×20 in), including for example, from about 2.5 cm×2.5 cm (1 in×1 in), from about 5.0 cm×5.0 cm (2 in×2 in), from about 7.5 cm×7.5 cm (3 in×3 in), and including about 12.5 cm×17.5 cm (5 in×7 in), and including about 10 cm×12.5 cm (4 in×5 in).

The non-woven graft materials typically have a thickness ranging from about 0.1 mm to about 5 mm, including from about 0.3 mm to about 0.8 mm, about 0.3 mm to about 0.7 mm, and about 0.3 mm to about 0.5 mm The non-woven graft material is typically microporous, and has interconnecting pores having a pore size in the range of from about 10 $\mu m^2$ to about 10,000 $\mu m^2$. Particularly suitable embodiments have a pore size of less than 300 $\mu m^2$. It is believed that pores of this size range can accommodate penetration by cells and can support the growth and proliferation of cells, followed by vascularization and tissue development.

Figure 2:
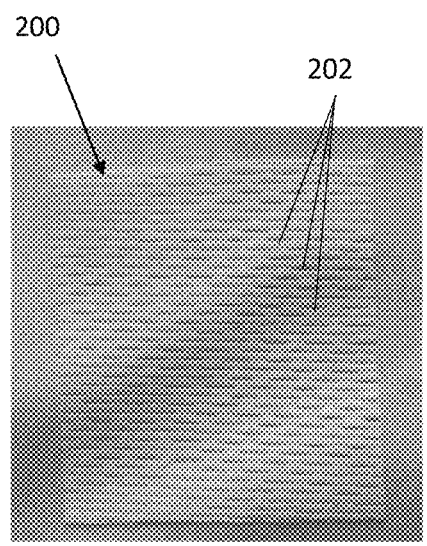
FIG. 2 illustrates an embodiment of a macro and microporous sheet of hybrid-scale fiber matrix.
Figure 3:
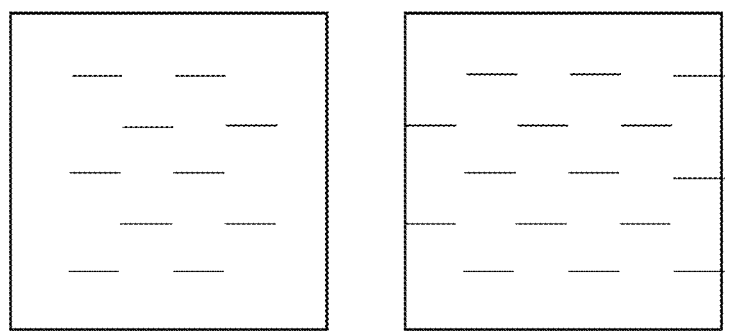
FIGS. 3-10 illustrate different embodiments of macroporous patterns.
Figure 4:
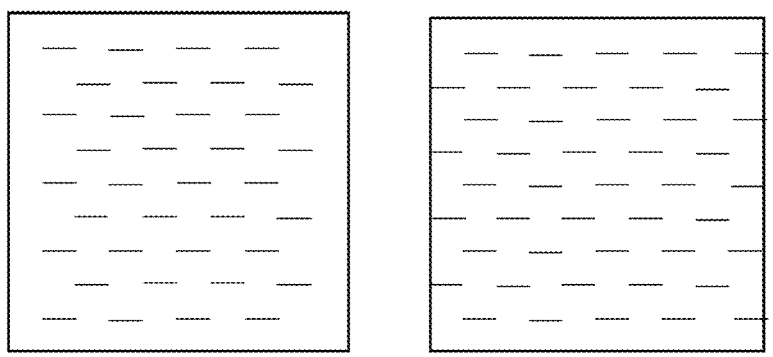
Figure 5:
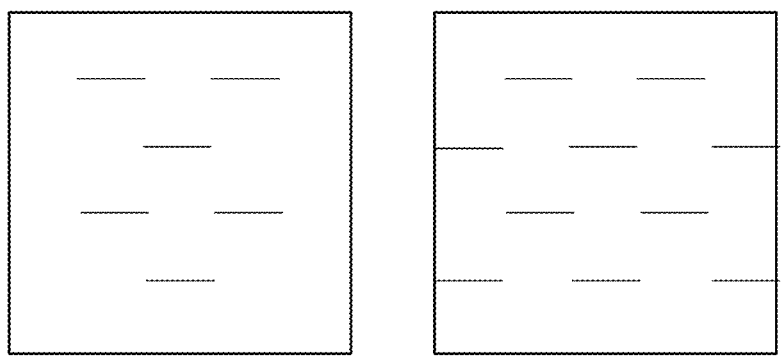
Figure 6:
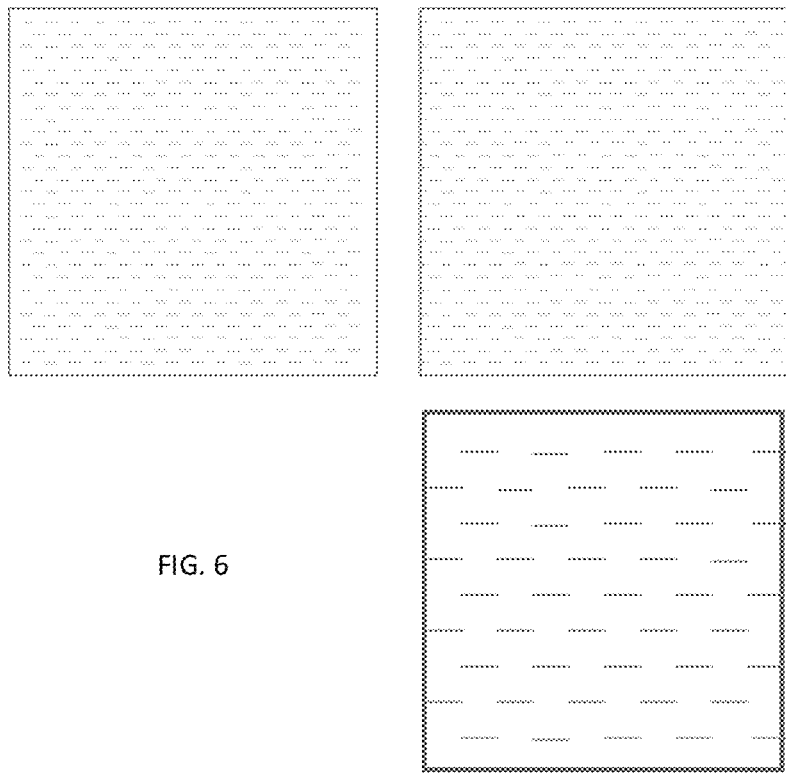
Figure 7:
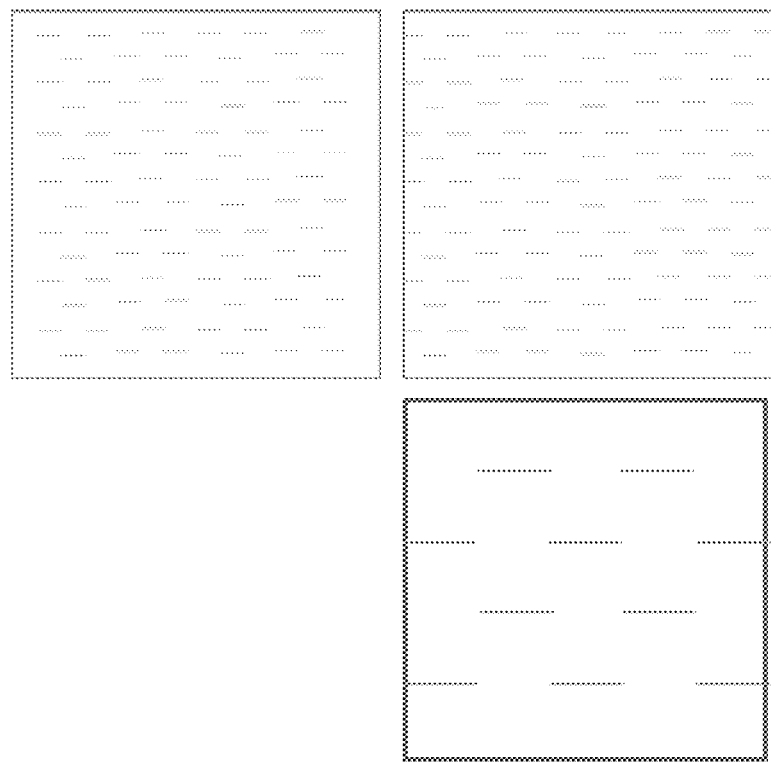
Figure 8:
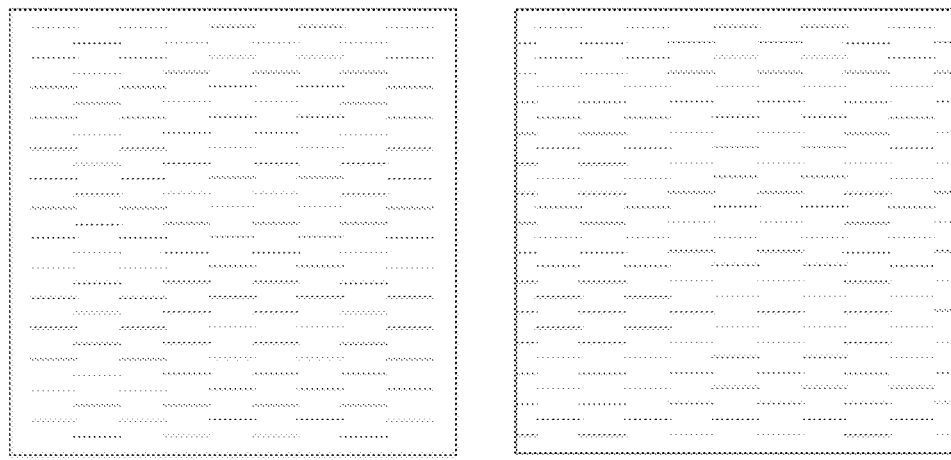
Figure 9:
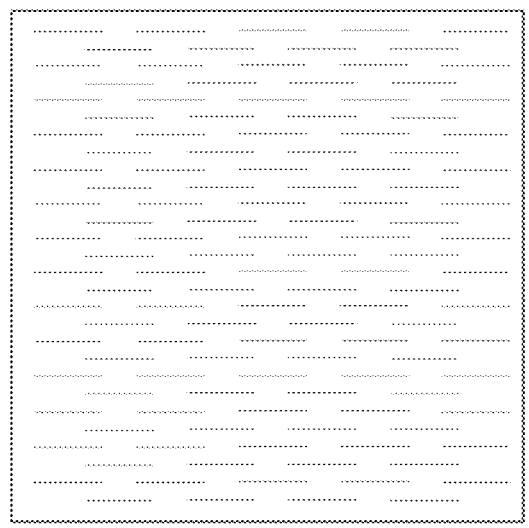
Figure 10:
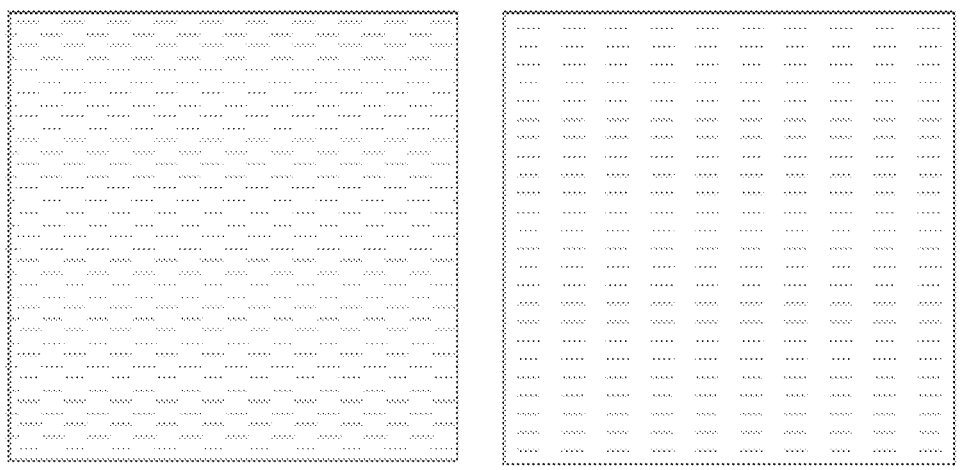

Additionally, as shown in FIG. 2, the material can be macroporous as well as microporous. Thus, the non-woven hybrid-scale fiber matrix graft material sheet 200 can include one or more perforations (e.g., holes, cuts, slots, slits, apertures) 202 in the sheet 200. In some embodiments, the perforations 202 can be found over the entire sheet 200. In some embodiments, the perforations 202 may be formed only in a portion of the sheet 200, such as 25%, 50%, or 75% of the sheet 200. The sections with perforations 202 may be separated or connected. In some embodiments, the perforations 202 can be uniform, though in alternative embodiments they may not be. In some embodiments, the perforations 202 are generally equally distributed throughout the sheet 200, which can provide equal distribution of fluid transport. In some embodiments, the perforations 202 can be concentrated in a certain area of the sheet 200, thus making specific areas more capable of fluid transport than other areas. In some embodiments, the density of slits in the non-woven hybrid-scale fiber matrix graft material sheet may range from 1 to 400 slits per square inch. In some embodiments, the slits in the non-woven hybrid-scale fiber matrix graft material may comprise a density of about 1 slit per square inch, about 5 slits per square inch, about 10 slits per square inch, about 15 slits per square inch, about 20 slits per square inch, about 40 slits per square inch, about 60 slits per square inch, about 80 slits per square inch, about 100 slits per square inch, about 150 slits per square inch, about 200 slits per square inch, about 250 slits per square inch, about 300 slits per square inch, about 350 slits per square inch, about 400 slits per square inch, and/or may comprise a density within a range defined by two of the aforementioned values. In some embodiments, the length of perforations in the non-woven hybrid-scale fiber matrix graft material sheet may range from 1-20 mm. In some embodiments, the length of perforations may be about 1 mm, about 2 mm, about 3 mm, about 5 mm, about 10 mm, about 15 mm, about 20 mm, and/or may comprise slits with lengths within a range defined by two of the aforementioned values. In some embodiments, perforations may be separated into rows, wherein the distance between each row may range between 0.5-20 mm. In some embodiments, the distance between each row may be about 0.5 mm, about 1 mm, about 2 mm, about 3 mm, about 5 mm, about 10 mm, about 15 mm, about 20 mm, and/or may comprise a distance within a range defined by two of the aforementioned values. In some embodiments, the distance between individual perforations in a row may range between 1-20 mm. In some embodiments, the distance between individual perforations may be about 1 mm, about 2 mm, about 3 mm, about 5 mm, about 10 mm, about 15 mm, about 20 mm, and/or may comprise distances within a range defined by two of the aforementioned values.

FIGS. 3-10 illustrate non-limiting various perforation patterns that could be used with embodiments of the disclosure.

Figure 11A:
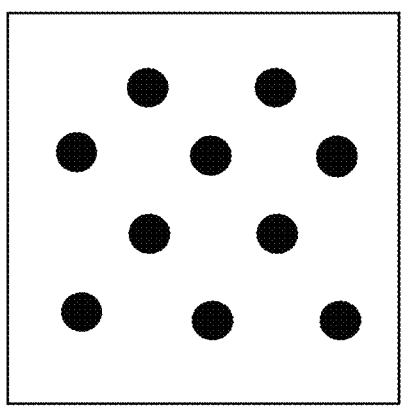
FIGS. 11A-11B illustrate example perforations for embodiments of the disclosure.
Figure 11B:
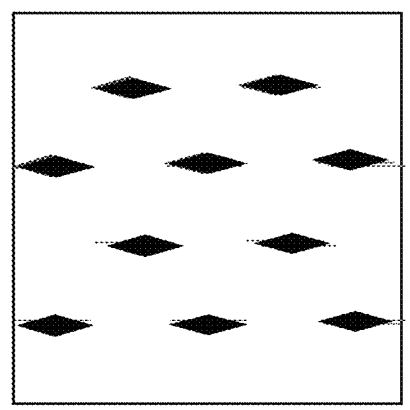
Figure 13A:
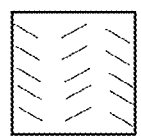
FIGS. 13A-13E illustrate example perforations for embodiments of the disclosure.
Figure 13B:
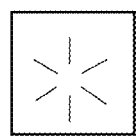
Figure 13C:
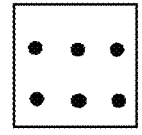
Figure 13D:
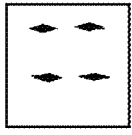
Figure 13E:
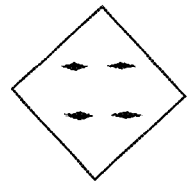

Further, while the previous FIGS. illustrate the perforations as straight line cuts, other types of perforations can be used as well. FIGS. 11A-11B illustrate some examples of alternate perforations using circles (FIG. 11A) and diamonds (FIG. 11B). These are not limiting shapes, and other shapes can be used as well for the perforations, such as triangles, rectangles, ovals, irregular polymers, etc. Further, combinations of different types of perforations can also be used. FIGS. 13A-13E also disclose non-limiting example perforation patterns, including combinations of perforations to create chevrons and stars, as well as irregular shapes.

Figure 14A:
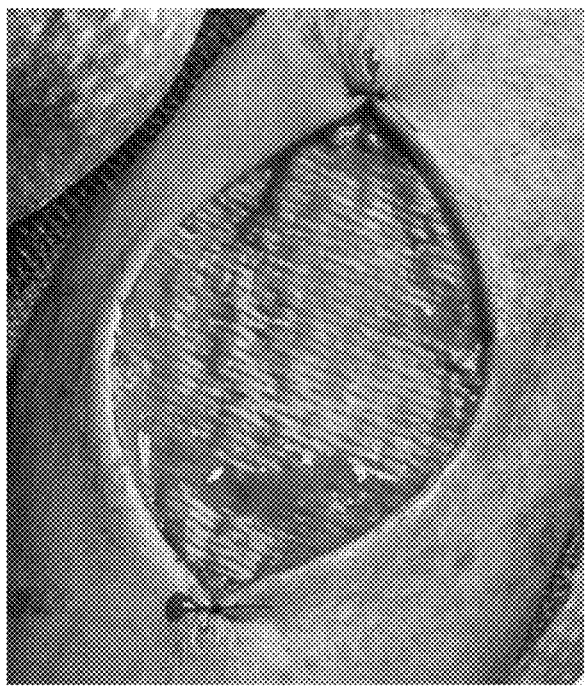
FIGS. 14A-14B illustrates example skin wounds. 14A illustrates a skin wound created by a laceration, while 14B illustrates a skin wound with avulsion and a meshed hybrid-scale fiber matrix covering.
Figure 14B:
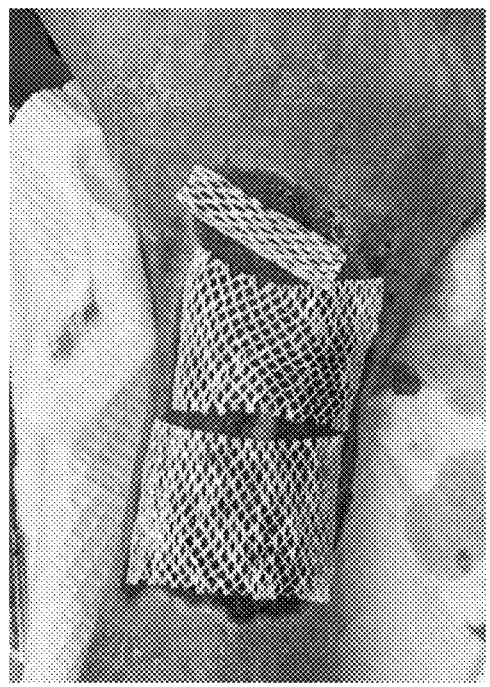
Figure 15:
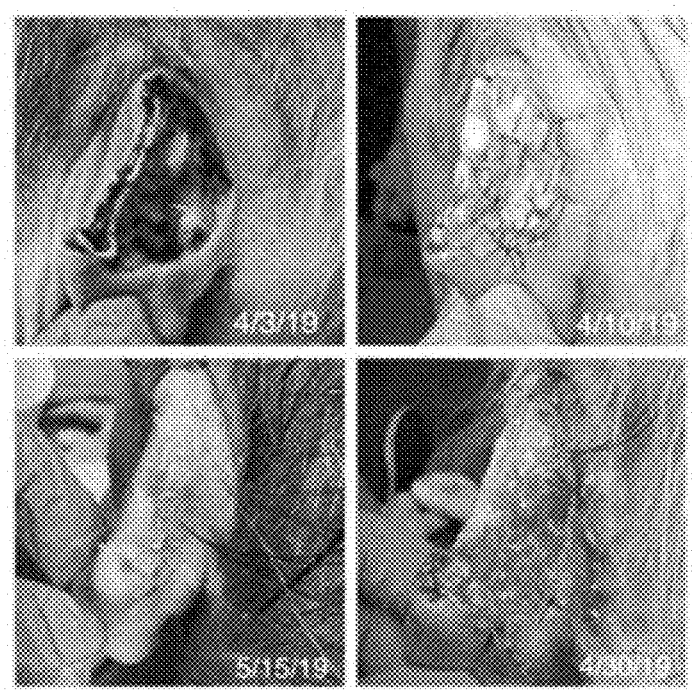
FIG. 15 illustrates an example skin wound and subsequent healing process over time.
Figure 16:
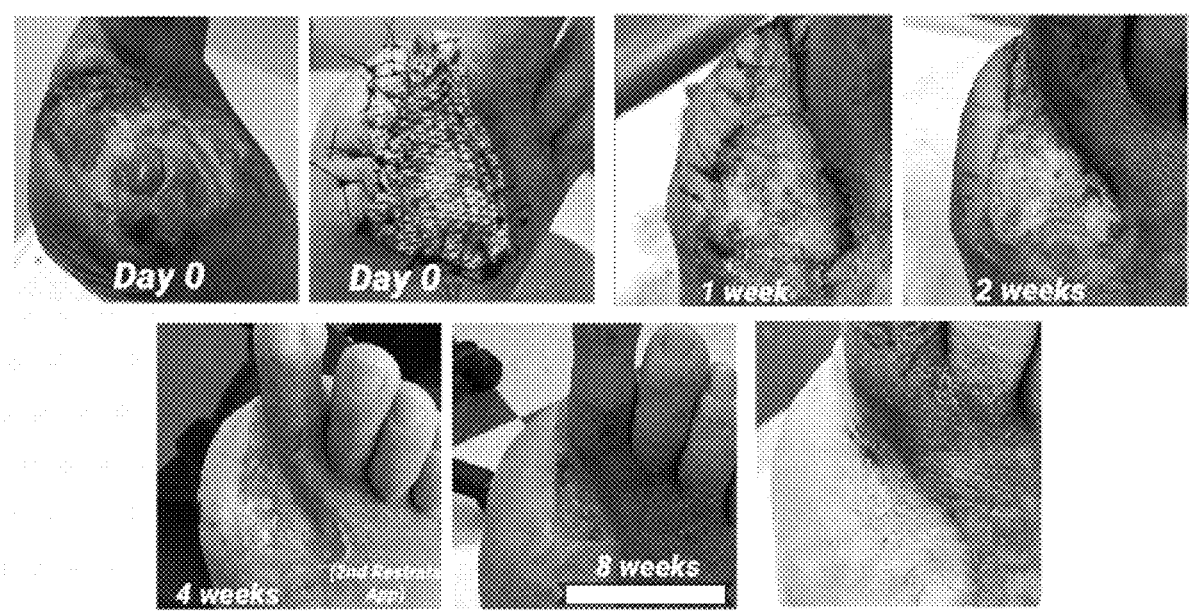
FIG. 16 illustrates an example skin wound and progression of healing over time.

FIGS. 12A-12D illustrate embodiments of a macro and micro porous matrix as discussed herein. FIG. 12A illustrates a representational top view of an embodiment of the macro and micro porous matrix with dimensions of 3±0.05 inches by 1±0.05 inches. In FIG. 12A, the matrix is comprised of two fiber populations created by an electrospinning process wherein the first fiber population is a copolymer between glycolide and L-lactide, while the second fiber population is a polymer of paradioxanone. FIG. 12A further features a recurring pattern, featuring circular protrusions and perforations represented as white lines recurring over a substantial portion of the matrix. FIG. 12B is a depth representation side view of an embodiment of the macro and micro porous matrix, showing overall thickness of the matrix, ranging between 0.2 and 0.95 mm. FIG. 12. C illustrates a representational top view of an embodiment of the macro and micro porous matrix with dimensions of 3±0.05 inches by 1±0.05 inches. FIG. 12C features matrix is comprised of two fiber populations created by an electrospinning process wherein the first fiber population is a copolymer between glycolide and L-lactide, while the second fiber population is a polymer of paradioxanone. FIG. 12D is a depth representation side view of an embodiment of the macro and micro porous matrix, wherein the surface is substantially flat, or otherwise lacking in surface patterns. FIGS. 14A-14B, 15, and 16 illustrate non-limiting embodiments of the hybrid-scale fiber matrix as applied to tissue. FIGS. 14A and 14B illustrate a non-limiting embodiment wherein a non-woven graft material is overlaid onto a wound site.

In some aspects, the non-woven graft materials can be surface-modified with biomolecules such as (but not limited to) hyaluronans, collagen, laminin, fibronectin, growth factors, integrin peptides (Arg-Gly-Asp; i.e., RGD peptides), and the like, or by sodium hyaluronate and/or chitosan niacinamide ascorbate, which are believed to enhance cell migration and proliferation, or any combination thereof. The material can also be impregnated with these and other bioactive agents such as drugs, vitamins, growth factors, therapeutic peptides, and the like. In addition, drugs that would alleviate pain may also be incorporated into the material.

In another aspect, the present disclosure is directed to a laminate comprising a non-woven graft material, wherein the non-woven graft material includes a first non-woven fiber composition and a second non-woven fiber composition.

In some embodiments, the non-woven graft material of the laminate includes a first non-woven fiber composition including poly(lactic-co-glycolic acid) and a second non-woven fiber composition including polydioxanone, as described herein.

In some embodiments, the non-woven graft material can include at least one projection arising from a surface of the non-woven graft material. The projection is a protrusion or bulge arising from a surface of the non-woven graft material. The projection can arise from a top surface of the non-woven graft material, a bottom surface of the non-woven graft material, and a top surface and a bottom surface of the non-woven graft material. The projection can be any desired shape such as, for example, circular, spherical, square, rectangular, diamond, star, irregular, and combinations thereof. The projection can be any desired height as measured from the surface of the material to the top of the projection. In one embodiment, the projection can have a substantially uniform height from the surface of the material. In another embodiment, the projection can further form gradually from the surface of the material to the highest measurable surface of the projection. In some embodiments, a surface of the non-woven graft material includes a plurality of protrusions. The plurality of protrusions can be patterned or randomly distributed on a surface of the non-woven graft material. In another embodiment, the method includes forming at least one indentation in a surface of the non-woven graft material. The indentation is a recess or depression in a surface of the non-woven graft material. The indentation can in a top surface of the non-woven graft material, a bottom surface of the non-woven graft material, and a top surface and a bottom surface of the non-woven graft material. The indentation can be any desired shape such as, for example, circular, spherical, square, rectangular, diamond, star, irregular, and combinations thereof. The indentation can be any desired depth as measured from the surface of the material to the bottom of the indentation. In one embodiment, the indentation can have a substantially uniform depth from the surface of the material to the deepest depth of the indentation. In another embodiment, the indentation can further form gradually from the surface of the material to the deepest depth of the indentation. In some embodiments, a surface of the non-woven graft material includes a plurality of indentations. The plurality of indentations can be patterned or randomly distributed on a surface of the non-woven graft material. In another embodiment, the non-woven graft material can include at least one projection arising from a surface of the non-woven graft material and at least one indentation in the surface of the non-woven graft material. In another embodiment, the non-woven graft material can include at least one projection arising from a top surface of the non-woven graft material and at least one indentation in the top surface of the non-woven graft material. In another embodiment, the non-woven graft material can include at least one projection arising from a bottom surface of the non-woven graft material and at least one indentation in the bottom surface of the non-woven graft material. In another embodiment, the non-woven graft material can include at least one projection arising from a top surface of the non-woven graft material, at least one projection arising from a bottom surface of the non-woven graft material, at least one indentation in the top surface of the non-woven graft material, and at least one indentation in the bottom surface of the non-woven graft material. The plurality of indentations and the plurality of indentations can be patterned or randomly distributed on a surface of the non-woven graft material. Suitable methods for forming projections and indentations include pressing, stamping, and other methods known to those skilled in the art.

Electrospinning

In some embodiments, the present disclosure is directed to methods of preparing the non-woven graft materials. The methods generally include preparing aqueous solutions of the polymers described above. Particularly, fibers resulting from separate polymer solutions can be contacted together using one or more processes such as electrospinning, electrospraying, melt-blowing, spunbonding, to form the non-woven graft material; and drying the non-woven graft material.

The non-woven graft material is dried to remove solvents used to prepare the aqueous polymer solutions. Drying can be done using methods generally known in the art, including, without limitation, Yankee dryers, vacuum chambers, vacuum ovens, and through-air dryers. Preferably, a non-compressive drying method that tends to preserve the bulk or thickness of the non-woven graft material is employed. Suitable through-drying apparatus and through-drying fabrics are conventional and well-known. One skilled in the art can readily determine the optimum drying gas temperature and residence time for a particular through-drying operation.

In some embodiments, a first fiber composition resulting from a first aqueous polymer solution and a second fiber composition resulting from a second aqueous polymer solution are blended to form a non-woven graft material using the electrospinning process as described above. The electrospinning process generally involves applying a high voltage (e.g., about 1 kV to about 100 kV, including about 3 kV to about 80 kV, depending on the configuration of the electrospinning apparatus) to a polymer fiber solution to produce a polymer jet. As the jet travels in air, the jet is elongated under repulsive electrostatic force to produce nanofibers or hybrid-scale fibers from the polymer fiber solution. The high voltage is applied between the grounded surface (or oppositely charged surface) and a conducting capillary into which a polymer fiber solution is injected. The high voltage can also be applied to the solution or melt through a wire if the capillary is a nonconductor such as a glass pipette. Initially the solution at the open tip of the capillary is pulled into a conical shape (the so-called "Taylor cone") through the interplay of electrical force and surface tension. At a certain voltage range, a fine jet of polymer fiber solution forms at the tip of the Taylor cone and shoots toward the target. Forces from the electric field accelerate and stretch the jet. This stretching, together with evaporation of solvent molecules, causes the jet diameter to become smaller. As the jet diameter decreases, the charge density increases until electrostatic forces within the polymer overcome the cohesive forces holding the jet together (e.g., surface tension), causing the jet to split or "splay" into a multifilament of polymer nanofibers or hybrid-scale fibers. The fibers continue to splay until they reach the collector, where they are collected as nonwoven nanofibers or hybrid-scale fibers, and are optionally dried.

Suitable solvents for preparing aqueous polymer solutions include, for example, hexafluoroisopropanol (HFIP), dichloromethane (DCM), dimethylformamide (DMF), acetone, and ethanol.

In some embodiments, the method can further include forming at least one projection arising from a surface of the non-woven graft material, forming at least one indentation in a surface of the non-woven graft material, and combinations thereof. The projection is a protrusion or bulge arising from a surface of the non-woven graft material. The projection can arise from a top surface of the non-woven graft material, a bottom surface of the non-woven graft material, and a top surface and a bottom surface of the non-woven graft material. The projection can be any desired shape such as, for example, circular, spherical, square, rectangular, diamond, star, irregular, and combinations thereof. The projection can be any desired height as measured from the surface of the material to the top of the projection. In one embodiment, the projection can have a substantially uniform height from the surface of the material. In another embodiment, the projection can further form gradually from the surface of the material to the highest measurable surface of the projection. In some embodiments, a surface of the non-woven graft material includes a plurality of protrusions. The plurality of protrusions can be patterned or randomly distributed on a surface of the non-woven graft material. In another embodiment, the method includes forming at least one indentation in a surface of the non-woven graft material. The indentation is a recess or depression in a surface of the non-woven graft material. The indentation can in a top surface of the non-woven graft material, a bottom surface of the non-woven graft material, and a top surface and a bottom surface of the non-woven graft material. The indentation can be any desired shape such as, for example, circular, spherical, square, rectangular, diamond, star, irregular, and combinations thereof. The indentation can be any desired depth as measured from the surface of the material to the bottom of the indentation. In one embodiment, the indentation can have a substantially uniform depth from the surface of the material to the deepest depth of the indentation. In another embodiment, the indentation can further form gradually from the surface of the material to the deepest depth of the indentation. In some embodiments, a surface of the non-woven graft material includes a plurality of indentations. The plurality of indentations can be patterned or randomly distributed on a surface of the non-woven graft material. In another embodiment, the non-woven graft material can include at least one projection arising from a surface of the non-woven graft material and at least one indentation in the surface of the non-woven graft material. In another embodiment, the non-woven graft material can include at least one projection arising from a top surface of the non-woven graft material and at least one indentation in the top surface of the non-woven graft material. In another embodiment, the non-woven graft material can include at least one projection arising from a bottom surface of the non-woven graft material and at least one indentation in the bottom surface of the non-woven graft material. In another embodiment, the non-woven graft material can include at least one projection arising from a top surface of the non-woven graft material, at least one projection arising from a bottom surface of the non-woven graft material, at least one indentation in the top surface of the non-woven graft material, and at least one indentation in the bottom surface of the non-woven graft material. The plurality of indentations and the plurality of indentations can be patterned or randomly distributed on a surface of the non-woven graft material. Suitable methods for forming projections and indentations include pressing, stamping, and other methods known to those skilled in the art.

In some embodiments, once the material has been electrospun, the macro perforations discussed above can be incorporated into the sheets of material, such as through a cutting step. This can be done mechanically, electronically, and/or computer controlled to provide for consistency in some embodiments. Laser cutting could also be used to create the perforations in the material.

In some embodiments, the perforations may be incorporated into the material during the electrospinning process, and thus no additional cutting step may be used. For example, a substrate pattern can be prepared so that when the fibers are electrospun onto the substrate, they leave a particular perforation pattern in the material. For example, the substrate can be metallic, and the fibers can stick to the metallic substrate to form the desired cut pattern.

In some embodiments, the sheets can be manufactured to have areas of higher or lower density of fibers, which can provide the macroporous abilities discussed herein.

Tissue Repair

In some embodiments, the present disclosure is directed to a method of tissue repair in an individual in need thereof. The method can include: applying a non-woven graft material to a surgical field, wherein the non-woven graft material comprises a first fiber composition and a second fiber composition. The method is particularly suitable for repairing tissues such as, for example, dura mater, pericardium, small intestinal submucosa, dermis, epidermis, tendon, trachea, heart valve leaflet, gastrointestinal tract, and cardiac tissue. Suitable tissue repair procedures include, for example, neurosurgeries such as dura mater repair, skin grafts, tracheal repair, gastrointestinal tract repair (e.g., abdominal hernia repair, ulcer repair), cardiac defect repair, head and neck surgeries, application to bone fractures, and burn repair.

Suitably, the non-woven graft material includes a first fiber composition, wherein the first fiber composition includes a polymer selected from polycaprolactone (poly(ε-caprolactone), PCL), polydioxanone (PDO), poly (glycolic acid) (PGA), poly(L-lactic acid) (PLA), poly(lactid e-co-glycolide) (PLGA), poly(L-lactid e) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy) phosphazene] (PNmPh), poly(3-hydroxybutyrate-co-3-hydroxyvalerate) (PHBV), poly(ester urethane) urea (PEUU), poly (p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolid one; polystyrene (PS) and combinations thereof. Particularly suitable polymers include poly(lactic-co-glycolic acid), polydioxanone, polycaprolactone, and combinations thereof.

Suitably, the non-woven graft material includes a second fiber composition, wherein the second fiber composition includes a polymer selected from polycaprolactone (poly(c-caprolactone), PCL), polydioxanone (PDO), poly (glycolic acid) (PGA), poly(L-lactic acid) (PLA), poly(lactide-co-glycolide) (PLGA), poly(L-lactide) (PLLA), poly(D,L-1actide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly [bis(p-methylphenoxy) phosphazene] (PNmPh), poly(3-hydroxybutyrate-co-3-hydroxyvalerate) (PHBV), poly(ester urethane) urea (PEUU), poly(p-dioxanone) (PPDO), polyurethane (PU), polyethylene terephthalate (PET), poly(ethylene-co-vinylacetate) (PEVA), poly (ethylene oxide) (PEO), poly(phosphazene), poly(ethylene-co-vinyl alcohol), polymer nanoclay nanocomposites, poly (ethylenimine), poly(ethyleneoxide), poly vinylpyrrolid one; polystyrene (PS) and combinations thereof. Particularly suitable polymers include poly(lactic-co-glycolic acid), polydioxanone, polycaprolactone, and combinations thereof.

In a particularly suitable embodiment, the non-woven graft material includes a first fiber composition comprising poly(lactic-co-glycolic acid) and a second fiber composition comprising polydioxanone.

As used herein, "individual in need thereof" refers to an individual having a tissue defect, tissue damage, tissue that is missing due to damage or removal, and tissue damaged by incision. The methods are particularly suitable for use with an individual or subset of individuals having dura defects requiring repair of the dura mater. Individuals having dura defects can be those having a perforation in the dura mater, those having dura mater removed, those having damaged dura mater, and those having dura mater with a surgical incision. The individual in need thereof can be an adult individual, a child, and a pediatric individual. Particularly suitable individuals can be a human. Other particularly suitable individuals can be animals such as primates, pigs, dogs, cats, rabbits, rodents (e.g., mice and rats), and the like.

In some embodiments, the non-woven graft material is secured to the surgical field, such as by suturing the non-woven graft material to the surgical field. In other embodiments, the non-woven graft material is secured to the surgical field, such as by a surgical adhesive.

From the foregoing description, it will be appreciated that inventive nano-fiber and hybrid-scale fiber matrixes and methods of manufacturing and use are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any sub combination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount. Additionally, all values of tables within the disclosure are understood to either be the stated values or, alternatively, about the stated value.

The disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A three-dimensional electrospun hybrid-scale fiber matrix synthetic skin graft for use in repairing tissue for wound care, the three-dimensional hybrid-scale fiber matrix synthetic skin graft comprising:

a flexible electrospun fiber network, the flexible electrospun fiber network comprising:

a first set of electrospun fibers comprising a first bioresorbable polymer; and a second set of electrospun fibers comprising a second bioresorbable polymer, wherein the first bioresorbable polymer comprises a different composition from the second bioresorbable polymer;

the flexible electrospun fiber network further comprising one or more macro-scale pores and one or more micro-scale pores, the one or more macro-scale pores comprising an opening of about 1 mm to about 20 mm, and the one or more micro-scale pores comprising an opening with areas of about 10 $\mu m^2$ to less than 300 $\mu m^2$, wherein the three-dimensional electrospun hybrid-scale fiber matrix synthetic skin graft is sufficiently flexible to facilitate application of the three-dimensional electrospun hybrid-scale fiber matrix synthetic skin graft to uneven surfaces of the tissue, wherein the three-dimensional electrospun hybrid-scale fiber matrix synthetic skin graft is sufficiently flexible to enable movement of the three-dimensional electrospun hybrid-scale fiber matrix synthetic skin graft by the tissue, wherein the first set of electrospun fibers comprise an average diameter less than 10 micrometers, and wherein the first set of electrospun fibers and the second set of electrospun fibers are configured to degrade after application to the tissue.

2. The three-dimensional electrospun hybrid-scale fiber matrix, synthetic skin graft of claim 1, wherein the one or more macro-scale pores of the three-dimensional electrospun hybrid-scale fiber matrix synthetic skin graft are configured to allow flow through of an exudate.

3. The three-dimensional electrospun hybrid-scale fiber matrix synthetic skin graft of claim 1, wherein the one or more micro-scale pores of the three-dimensional electrospun hybrid-scale fiber matrix synthetic skin graft are configured to facilitate cell growth.

4. The three-dimensional electrospun hybrid-scale fiber matrix synthetic skin graft of claim 1, wherein the first bioresorbable polymer comprises poly(lactic-co-glycolic acid), and wherein the second bioresorbable polymer comprises polydioxanone.

5. The three-dimensional electrospun hybrid-scale fiber matrix synthetic akin graft of claim 1, wherein perforations are distributed equally throughout the matrix.

6. The three-dimensional electrospun hybrid-scale fiber matrix synthetic skin graft of claim 1, wherein the first structure of fibers comprises an average diameter Dot greater than 2,000 nanometers.

7. The three-dimensional electrospun hybrid-scale fiber matrix synthetic skin graft of claim 1, wherein the three-dimensional electrospun hybrid-scale fiber matrix synthetic skin graft comprises a plurality of protrusions arising from a bottom surface of the flexible electrospun fiber network and a plurality of indentations in a top surface of the flexible electrospun fiber network, wherein the plurality of protrusions arising from the bottom surface comprise a substantially uniform height, wherein the plurality of indentations arising from the top surface comprise a substantially uniform depth, wherein the plurality of protrusions and the plurality of indentations are spherical, wherein the plurality of protrusions are patterned throughout the bottom surface, wherein the plurality of indentations are patterned throughout the top surface.

8. The three-dimensional electrospun hybrid-scale fiber matrix synthetic skin graft of claim 1, wherein the one or more macro-scale pores comprise slits through a full thickness of the three-dimensional hybrid-scale fiber matrix synthetic skin graft with a density of at least 5 slits per square inch.

9. A method of manufacturing a biomedical patch device for tissue repair, the method comprising:
depositing a first structure of fibers having electrospun hybrid-scale fibers via electrospinning, the first structure of fibers configured to promote cell growth; and
depositing a second structure of fibers having electrospun hybrid-scale fibers via electrospinning, the second structure of fibers configured to promote cell growth, the first structure of fibers comprising a different composition from the second structure of fibers;
the first structure of fibers and the second structure of fibers comprising one or more macro-scale pores and one or more micro-scale pores, the one or more macro-scale pores comprising an opening of about 1 mm to about 20 mm, and the one or more micro-scale pores comprising an opening with areas of about 10 $\mu m^2$ to less than 300 $\mu m^2$; the biomedical patch device comprising a surface, wherein the surface comprises a surface pattern configured to contact tissue, wherein the surface pattern, the first structure of fibers, and the second structure of fibers are configured to promote cell growth in one or more defined directions,
the biomedical patch device sufficiently flexible to facilitate application of the biomedical patch device to even surfaces of the tissue,
the biomedical patch device sufficiently flexible to enable movement of the biomedical patch device with the tissue,
wherein the first structure of fibers comprise an average diameter less than 10 micrometers, and
wherein the first structure of fibers and the second structure of fibers are configured to degrade after application to the tissue.

10. The method of claim 9, wherein a first portion of the biomedical patch of a particular size comprises a higher number of fibers than a second portion of the biomedical patch of the particular size.

11. The method of claim 9, wherein the surface pattern is formed by positioning a mask between a collector and a spinneret, wherein the mask is configured to prevent depositing at least some of the first structure of fibers or the second structure of fibers on the collector.

12. The method of claim 9, wherein the surface pattern is formed by depositing the first structure of fibers and the second structure of fibers directly on a collector without a mask.

13. The method of claim 12, wherein the surface pattern comprises a plurality of organized features.

14. The method of claim 12, wherein the surface pattern comprises a plurality of topographical features configured to further promote migration of cells in one or more of the plurality of defined directions.

15. The method of claim 9, wherein the macro-scale pores are generated through cutting mechanically, electronically, and/or computer controlled.

16. The method of claim 15, wherein the cutting is laser cutting.

17. The method of claim 9, wherein the first structure of fibers comprises an average diameter not greater than 2,000 nanometers.

18. The method of claim 9, wherein the surface comprises a top surface and a bottom surface, and wherein the biomedical patch device comprises a plurality of protrusions arising from the bottom surface and a plurality of indentations on the top surface, wherein the plurality of protrusions comprise a substantially uniform height, wherein the plurality of indentations arising from the top surface comprise a substantially uniform depth, wherein the plurality of protrusions and the plurality of indentations are spherical, wherein the plurality of protrusions are patterned throughout the bottom surface, wherein the plurality of indentations are patterned throughout the top surface.

19. The method of claim 9 further comprising forming the one or more macro-scale pores as slits through a full thickness of the three-dimensional hybrid-scale fiber matrix synthetic skin graft with a density of at least 5 slits per square inch.

* * * * *